US012773406B2

(12) United States Patent
Kim et al.

(10) Patent No.: US 12,773,406 B2
(45) Date of Patent: Oct. 27, 2026

(54) PHARMACEUTICAL COMPOSITION FOR PREVENTION OR TREATMENT OF NONALCOHOLIC STEATOHEPATITIS

(71) Applicant: DONG-A ST CO., LTD., Seoul (KR)

(72) Inventors: Mi-Kyung Kim, Gyeonggi-do (KR); Hansu Park, Gyeonggi-do (KR); Seung Ho Lee, Gyeonggi-do (KR)

(73) Assignee: Dong-A St Co., Ltd. (KR)

( * ) Notice: Subject to any disclaimer, the term of this patent is extended or adjusted under 35 U.S.C. 154(b) by 796 days.

(21) Appl. No.: 17/905,912

(22) PCT Filed: Mar. 10, 2021

(86) PCT No.: PCT/KR2021/002989
§ 371 (c)(1),
(2) Date: Sep. 8, 2022

(87) PCT Pub. No.: WO2021/182876
PCT Pub. Date: Sep. 16, 2021

(65) Prior Publication Data

US 2023/0117286 A1 Apr. 20, 2023

(30) Foreign Application Priority Data

Mar. 11, 2020 (KR) ........................ 10-2020-0030423

(51) Int. Cl.

| | |
|---|---|
| ***A61K 31/506*** | (2006.01) |
| ***A61K 31/192*** | (2006.01) |
| ***A61K 31/495*** | (2006.01) |
| ***A61K 31/4985*** | (2006.01) |
| ***A61K 31/519*** | (2006.01) |
| ***A61K 31/55*** | (2006.01) |
| ***A61K 31/575*** | (2006.01) |
| ***A61P 1/16*** | (2006.01) |

(52) U.S. Cl.
CPC .......... *A61K 31/506* (2013.01); *A61K 31/192* (2013.01); *A61K 31/495* (2013.01); *A61K 31/4985* (2013.01); *A61K 31/519* (2013.01); *A61K 31/55* (2013.01); *A61K 31/575* (2013.01); *A61P 1/16* (2018.01)

(58) Field of Classification Search
CPC .................................................... A61K 31/506
USPC .......................................................... 514/171
See application file for complete search history.

(56) References Cited

U.S. PATENT DOCUMENTS

| | | | | |
|---|---|---|---|---|
| 9,895,370 | B2 | 2/2018 | Kang et al. | |
| 10,428,055 | B2 | 10/2019 | Yang et al. | |
| 12,115,159 | B2 * | 10/2024 | Kim | A61P 1/06 |
| 2006/0154866 | A1 | 7/2006 | Chu et al. | |
| 2011/0212939 | A1 | 9/2011 | Bertram et al. | |
| 2012/0053180 | A1 | 3/2012 | Kang et al. | |
| 2013/0310331 | A1 | 11/2013 | Joubert et al. | |
| 2014/0051714 | A1 | 2/2014 | Jones | |
| 2015/0322128 | A1 | 11/2015 | Bossart et al. | |
| 2017/0049773 | A1 | 2/2017 | Kang et al. | |
| 2019/0008864 | A1 | 1/2019 | Kang et al. | |
| 2019/0092763 | A1 | 3/2019 | Yang et al. | |
| 2020/0071306 | A1 | 3/2020 | Esler et al. | |
| 2021/0330748 | A1 | 10/2021 | Linder et al. | |
| 2021/0361629 | A1 | 11/2021 | Colca | |
| 2022/0047591 | A1 * | 2/2022 | Kim | A61K 31/454 |
| 2023/0143119 | A1 | 5/2023 | Kim et al. | |

FOREIGN PATENT DOCUMENTS

| | | | |
|---|---|---|---|
| CA | 2959714 | | 5/2016 |
| CA | 3113579 | | 3/2020 |
| CA | 3167630 | | 9/2021 |
| CA | 3168474 | | 9/2021 |
| CN | 101128192 | A | 2/2008 |
| CN | 107074838 | A | 8/2017 |
| CN | 106459170 | B | 8/2020 |
| CN | 115461072 | A | 12/2022 |
| EA | 025484 | B1 | 12/2016 |
| EP | 1808168 | A1 | 7/2007 |
| EP | 3212640 | | 9/2017 |
| EP | 3263134 | | 1/2018 |
| EP | 3827829 | | 6/2021 |
| JP | 2008-526235 | A | 7/2008 |
| JP | 2013-538862 | A | 10/2013 |
| JP | 2017-517483 | A | 6/2017 |
| JP | 2017-533213 | | 11/2017 |
| JP | 2019-534311 | | 11/2019 |
| KR | 10-2007- 0095400 | A | 9/2007 |

(Continued)

OTHER PUBLICATIONS

Stefan et al., The Metabolically Benign and Malignant Fatty Liver, Perspective in Diabetes, 2011, vol. 60, pp. 2011-2017. (Year: 2011).*
Bahirat et al., “Combination of APD668, a G protein-coupled receptor 119 agonist with linagliptin, a DPPIV inhibitor, prevents progression of steatohepatitis in a murine model of non-alcoholic steatohepatitis with diabetes,” 2018, Medical Molecular Morphology, 8 pages.
Office Action in Japanese Appln. No. 2022-554635, mailed on Sep. 13, 2023, 13 pages (with English translation).
Yang et al., “Therapeutic application of GPR119 ligands in metabolic disorders,” Diabetes, Obesity and Metabolism, 2018, 20:257-269.

(Continued)

*Primary Examiner* — Jeffrey H Murray
*Assistant Examiner* — Rilla Marie Samsell
(74) *Attorney, Agent, or Firm* — Fish & Richardson P.C.

(57) ABSTRACT

The present invention relates to a pharmaceutical composition for preventing or treating nonalcoholic fatty liver disease. The pharmaceutical composition according to the present invention exhibits excellent effects of improving lipid metabolism, reducing fat accumulation in liver tissues and inhibiting histological damage caused by inflammation and fibrosis of liver tissues, and thus can be effectively used as a use of preventing or treating nonalcoholic fatty liver disease.

18 Claims, 8 Drawing Sheets

(56) References Cited

FOREIGN PATENT DOCUMENTS

| | | | | |
|---|---|---|---|---|
| KR | 10-2015- 0018916 A | 2/2015 | | |
| KR | 10-2015-0088204 | 7/2015 | | |
| KR | 10-2016-0049434 | 5/2016 | | |
| KR | 10-2016- 0143724 A | 12/2016 | | |
| KR | 10-2017-0102299 | 9/2017 | | |
| KR | 10-2019-0040936 | 4/2019 | | |
| KR | 10-2019-0083659 | 7/2019 | | |
| KR | 10-2020- 0030469 A | 3/2020 | | |
| KR | 10-2021- 0114887 A | 9/2021 | | |
| RU | 2465896 C2 | 11/2012 | | |
| RU | 2012145116 A | 4/2014 | | |
| RU | 2670197 C1 | 10/2018 | | |
| RU | 2680527 | 2/2019 | | |
| SG | 11202101820 Y | 3/2021 | | |
| WO | WO 2006/076231 A2 | 7/2006 | | |
| WO | WO 2008/130584 A | 10/2008 | | |
| WO | WO 2010/004347 A1 | 1/2010 | | |
| WO | WO 2010/015664 A1 | 2/2010 | | |
| WO | WO 2011/118976 A1 | 9/2011 | | |
| WO | WO 2011113947 | 9/2011 | | |
| WO | WO 2012/006955 A1 | 1/2012 | | |
| WO | WO 2012/145604 A1 | 10/2012 | | |
| WO | WO 2015/020333 A1 | 2/2015 | | |
| WO | WO 2015/111971 A1 | 7/2015 | | |
| WO | WO 2015/155140 A1 | 10/2015 | | |
| WO | WO 2016068453 | 5/2016 | | |
| WO | WO-2016068453 A1 * | 5/2016 | ................ | A61P 3/10 |
| WO | WO 2016112305 | 7/2016 | | |
| WO | WO 2017/106112 A1 | 6/2017 | | |
| WO | WO 2017205684 | 11/2017 | | |
| WO | WO 2018087599 | 5/2018 | | |
| WO | WO 2018/153849 A1 | 8/2018 | | |
| WO | WO 2020014460 | 1/2020 | | |
| WO | WO 2020055170 | 3/2020 | | |
| WO | WO 2020/102337 A1 | 5/2020 | | |
| WO | WO-2021005436 A1 * | 1/2021 | ................ | A61P 3/10 |

OTHER PUBLICATIONS

Chalasani et al., "The diagnosis and management of non-alcoholic fatty liver disease: Practice Guideline by the American Association for the Study of Liver Diseases, American College of Gastroenterology, and the American Gastroenterological Association," Hepatology, 2012, 55(6):2005-2023.
Chou et al., "Quantitative analysis of dose-effect relationships: the combined effects of multiple drugs or enzyme inhibitors," Advances in Enzyme Regulation, 1984, 22:27-55.
International Search Report in International Appln. No. PCT/KR2021/002989, dated Jun. 24, 2021, 10 pages (with English Translation).
Yang et al., "GPR119: a promising target for nonalcoholic fatty liver disease," The FASEB Journal, 2016, 30(1):324-335.
Yang, "Inhibition of hepatic steatosis and fibrosis by GPR119 ligands," Doctor of Pharmacy Dissertation, Seoul National University Graduate School, Department of Pharmacy and Pharmacology, Aug. 2015, 131 pages (English Abstract on p. 105).
Younossi et al., "Nonalcoholic steatohepatitis is the fastest growing cause of hepatocellular carcinoma in liver transplant candidates," Clinical Gastroenterology and Hepatology, 2019, 17(4):748-755.
Bahirat, et al., "Co-administration of APD668, a G protein-coupled receptor 119 agonist and linagliptin, a DPPIV inhibitor, prevents progression of steatohepatitis in mice fed on a high trans-fat diet," Biochemical and Biophysical Research Communications, 2017, https://doi.org/10.1016/j.bbrc.2017.12.004, 6 pages.
IN Office Action in Indian Appln. No. 202237057640, dated Feb. 17, 2023, 7 pages (with English Translation).
Kharkevich, D.A., Pharmacology: Textbook, 2010, 10th ed., M.: GEOTAR-Media, pp. 72-82 (with English Translation).
Kholodov, L.E. et al., Clinical Pharmacokinetics, Moscow "Medicine," 1985, pp. 83-98, 134-138, 160, and 378-380 (with English Translation).
KR Notice of Allowance in Korean Appln. No. 10-2021-0031530, dated Feb. 27, 2023, 10 pages (with English Translation).
RU Office Action and Search Report in Russian Appln. No. 2022126303, dated Apr. 24, 2023, 19 pages (with English Translation).
Sergeev, P.V., Short Course of Molecular Pharmacology, The Ministry of Health Care of the Russian Soviet Federative Socialist Republic, 1975, p. 10 (with English Translation).
STN Database Search Report from Requesting Accelerated Examination in Korean Appln. No. 10-2021-0031530, dated Nov. 18, 2022, 16 pages.
Vengerovsky, A.I., Pharmacological Incompatibility, Lecture for Doctors, Scientific and Educational Process: Methodical Seminar, Bulletin of Siberian Medicine, 2003, 3:49-56 (with English Translation).
Office Action in Singapore Appln. No. 11202252580D, mailed on Sep. 2, 2024, 13 pages.
Sumida et al., "Antidiabetic Therapy in the Treatment of Nonalcoholic Steatohepatitis," International Journal of Molecular Sciences, Mar. 11, 2020, vol. 21, No. 6, Article No. 1907, pp. 1-22.
Ansarullah, "Stimulating β-cell regeneration by combining a GPR119 agonist with a DPP-IV inhibitor," PLoS One, 2013, available online Jan. 29, 2013, 8(1):e53345, 11 pages.
Office Action (Notification of Rejection) in Chinese Appln. No. 202180019128.0, mailed on Oct. 23, 2024, 16 pages (with English translation).
Marki et al., "Emerging role of obeticholic acid in the management of nonalcoholic fatty liver disease," World J Gastroenterol, Nov. 7, 2016, 22(41):9039-9043.
Office Action in New Zealand Appln. No. 791393, mailed on Mar. 28, 2025, 5 pages.
Office Action in New Zealand Appln. No. 791393, mailed on Sep. 19, 2024, 5 pages.
Friedman et al., "Mechanisms of NAFLD development and therapeutic strategies," Nat Med., 2018, 24(7):908-922.
Office Action in Chinese Appln. No. 2021800191280, mailed on Jan. 23, 2024, 16 pages (with English Translation).
[No Author], "A Study To Evaluate The Safety, Tolerability, PK and PD Of DA-1241 In Healthy Male Subjects, " ClinicalTrials.gov, Nov. 20, 2017, 11 pages, retrieved from https://clinicaltrials.gov/study/NCT03061981.
Bahirat et al., "APD668, a G protein-coupled receptor 119 agonist improves fat tolerance and attenuates fatty liver in high-trans fat diet induced steatohepatitis model in C57BL/6 mice," European Journal of Pharmacology, 2017, 801:35-45, doi: 10.1016/j.ejphar.2017.02.043.
BCBSIL Connect Team, "Diabetes: If you Can't Prevent It, You May Be able to Delay it," Blue Cross Blue Shield, Oct. 2023, 3 pages.
Belikov's Pharmaceutical Chemistry, 4th ed., 2007, MEDpress-inform, Moscow, pp. 27-29 (with English Translation).
Dyson G. & May P.'s Chemistry of Synthetic Drugs, translated from English. Mir, 1964, pp. 12-19 (with English Translation).
Extended European Search Report in European Appln. No. 19860397.9, mailed on May 6, 2022, 8 pages.
Extended European Search Report in European Appln. No. 21768861.3, mailed on Jan. 29, 2024, 10 pages.
Green et al., "Effect of Sitagliptin on cardiovascular Outcomes in Type 2 Diabetes", The New England Journal of Medicine, Jul. 15, 2016 (Year: 2016).
Hu et al., "A lincRNA-DYNLRB2-2/GPR119/GLP-1R/ABCA1-dependent signal transduction pathway is essential for the regulation of cholesterol homeostasis", Journal of Lipid Research, vol. 55, 2014, pp. 681-697.
International Search Report in International Appln. No. PCT/IB204/060898, mailed on Mar. 20, 2025, 9 pages (with English translation).
International Search Report in International Appln. No. PCT/KR2019/011839, mailed on Jan. 2, 2020, 3 pages.
International Search Report in International Appln. No. PCT/KR2021/002990, mailed on Jun. 24, 2021, 12 pages (with English Translation).
Jun, "Practice Guideline for the Diagnosis and Management of Non-alcoholic Fatty Liver Disease", Korean J. Gastroenterol. Vol. 60, No. 1, pp. 64-66 (with English Abstract).

(56) References Cited

OTHER PUBLICATIONS

Kato et al., "Safety and Pharmacokinetics of DS-8500a, a Novel GPR119 Agonist, After Multiple Oral Doses in Healthy Japanese Males," Clin Drug Investig., Jun. 2018, 38(6):519-525.
Kim et al., "A novel GPR119 agonist DA-1241 preserves pancreatic function via the suppression of ER stress and increased PDX1 expression," Biomedicine & Pharmacotherapy, 2021, 144:112324.
Knunyants et al., Chemical Encyclopedic Dictionary, Moscow, Soviet Encyclopedia, 1983, pp. 130-131 & 533-534.
Mantovani et al., "GLP-1 receptor agonists for NAFLD treatment in patients with an without type 2 diabetes: an upmailed on meta-analysis, " Exploration of Medicine, Jun. 2020, 1:108-123.
Marsilio et al., "Drug incompatibilities in the adult intensive care unit of a university hospital," Rev Bras Ter Intensiva., April-Jun. 2016, 28(2):147-153.
Office Action and Search Report in Russian Appln. No. 2021109691, mailed on Sep. 17, 2021, 27 pages (with English Translation).
Office Action and Search Report in Russian Appln. No. 2022124765, mailed on Apr. 10, 2023, 25 pages (with English Translation).
Office Action in Australian Appln. No. 2019337286, mailed on Feb. 3, 2022, 10 pages.
Office Action in Australian Appln. No. 2021235294, mailed on Sep. 12, 2023, 4 pages.
Office Action in Chinese Appln. No. 201980059145.X, mailed on Mar. 24, 2023, 19 pages (with English Translation).
Office Action in Chinese Appln. No. 202180019079.0, mailed on Jan. 20, 2024, 16 pages (with English Translation).
Office Action in Indian Appln. No. 202137016429, mailed on Jun. 8, 2021, 5 pages (with English Translation).
Office Action in Japanese Appln. No. 2021-513203, mailed on Apr. 13, 2022, 8 pages (with English Translation).
Office Action in Japanese Appln. No. 2022-554634, mailed on Sep. 6, 2023, 11 pages (with English translation).
Office Action in Korean Appln. No. 10-2019-0112561, mailed on Nov. 12, 2020, 10 pages (with English Translation).
Office Action in Korean Appln. No. 10-2024-0072704, mailed on May 8, 2026, 14 pages (with English translation).
Office Action in Saudi Arabian Appln. No. 522440429, mailed on Mar. 22, 2023, 11 pages (with English Translation).
Office Action in Singapore Appln. No. 11202252170H, mailed on Sep. 2, 2024, 13 pages.
Smirnova et al., "Optical isomerism and biological activity of pharmaceutical preparations," Bulletin of Moscow University, Series 2 Chemistry, 2012, 53(3): 147-156 (with English Translation).
Verma et al., "Predictive value of ALT levels for non-alcoholic steatohepatitis (NASH) and advanced fibrosis in non-alcoholic fatty liver disease (NAFLD), " Liver International, 2013, 1398-1405.
Wang et al., "Effects of glucagon-like peptide-1 receptor agonists on non-alcoholic fatty liver disease and inflammation," World Journal of Gastroenterology, Oct. 2014, 20(40):14821-14830.

* cited by examiner

***, p < 0.001 vs NASH Co.
, p < 0.001 vs Combo

***, p < 0.001 vs NASH Co.
& ###, p < 0.05 & p < 0.001 vs Combo

| Treatment | | GPR119 agonist | PPAR agonist | ACC inhibitor | FXR agonist |
|---|---|---|---|---|---|
| | | Compound 1 | Elafibranor | Firsocostat | Obeticholic Acid |
| $IC_{30}$ (μM) | Alone | 0.53 | 5.04 | 2.88 | 4.02 |
| | +0.3 μM Compd 1 | - | 0.59 | 0.04 | 1.85 |
| Combination Index (CI) | | - | **0.7** | **0.6** | **1.0** |

PHARMACEUTICAL COMPOSITION FOR PREVENTION OR TREATMENT OF NONALCOHOLIC STEATOHEPATITIS

RELATED APPLICATIONS

This application is a National Stage Application of International Application No. PCT/KR2021/002989, filed Mar. 10, 2021, which claims the benefit of South Korean Application No. 10-2020-0030423, filed Mar. 11, 2020, the entire contents of which applications are incorporated herein by reference in their entirety.

TECHNICAL FIELD

The present invention relates to a pharmaceutical composition for preventing or treating nonalcoholic fatty liver disease, including a G protein coupled receptor 119 (GPR119) agonist as an active ingredient and at least one drug of another mechanism.

BACKGROUND

Fatty liver is a pathological condition in which triglycerides are excessively accumulated in hepatocytes, and medically defined as a condition in which triglycerides account for 5% or more of a liver weight. Fatty liver is classified into alcoholic and nonalcoholic fatty livers depending on whether fatty liver is caused by excessive alcohol intake or not. Nonalcoholic fatty liver disease (NAFLD) is a group of diseases that encompass all aspects of the disease ranging from nonalcoholic fatty liver to steatohepatitis and cirrhosis. Simple nonalcoholic fatty liver is a disease in which only fat deposition in the liver is present, but without any findings about hepatocyte damage and fibrosis, and only fat deposition in liver tissues is increased due to insulin resistance, etc. Nonalcoholic fatty liver may progress into nonalcoholic steatohepatitis (NASH) accompanied by fibrosis due to hepatocyte damage caused by an inflammatory response according to oxidative stress or the like.

Unlike simple fatty liver, nonalcoholic steatohepatitis may progress into cirrhosis and liver cancer causing irreversible liver damage, thus increasing mortality associated with liver disease and overall mortality (Hepatology, 2012 (55):2005-2023). For this reason, as of 2013, nonalcoholic steatohepatitis was a second most common cause of liver transplantation after hepatitis C according to US statistical data. Since 2020, however, nonalcoholic steatohepatitis has been expected to become a first causative disease of liver transplantation rather than hepatitis C, and thus there is an urgent need for developing a drug for preventing and treating nonalcoholic steatohepatitis (Clinical Gastroenterology and Hepatology, 2019(17):748-755).

DETAILED DESCRIPTION OF THE INVENTION

Technical Problem

One object of the present invention is to provide a pharmaceutical composition for preventing or treating nonalcoholic steatohepatitis, which includes a compound represented by chemical Formula 1, pharmaceutically acceptable salts thereof, optical isomers thereof, hydrates thereof, solvates thereof, or mixtures thereof; and at least one selected from a PPAR agonist, a DPPIV inhibitor, an ACC inhibitor, a FXR agonist and a CCR2/5 dual antagonist.

Technical Solution

A pharmaceutical composition for preventing or treating nonalcoholic steatohepatitis according to one embodiment of the present invention may include a compound represented by chemical Formula 1 below, pharmaceutically acceptable salts thereof, optical isomers thereof, hydrates thereof, solvates thereof, or mixtures thereof; and at least one selected from a PPAR agonist, a DPPIV inhibitor, an ACC inhibitor, a FXR agonist and a CCR2/5 dual antagonist.

[Formula 1]

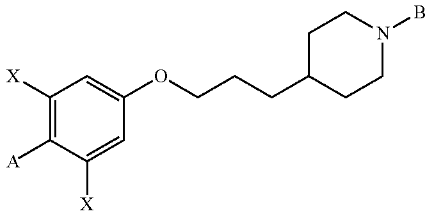

In above Formula 1, A may be an oxadiazole group, a dihydrooxazole group, a thiazole group or a thiadiazole group. Above A may be unsubstituted or substituted with at least one substituent selected from the group consisting of a halogen atom, a C1-C6 straight or branched chain alkyl group and a C1-C6 straight or branched chain hydroxyalkyl group. The alkyl group or the hydroxyalkyl group may be each independently unsubstituted or substituted with a halogen atom or a C1-C6 alkoxy group.

B may be a pyridine group, a pyrimidine group, a pyrazine group or an oxadiazole group. Above B may be unsubstituted or substituted with at least one substituent selected from the group consisting of a halogen atom, a C1-C6 straight or branched chain alkyl group, a C1-C6 straight or branched chain hydroxyalkyl group, a C1-C6 alkoxy group and an oxadiazole group. The C1-C6 straight or branched chain alkyl group, the C1-C6 straight or branched chain hydroxyalkyl group, the C1-C6 alkoxy group or the oxadiazole group may be each independently unsubstituted or substituted with halogen, a C1-C6 alkyl group or a C1-C6 alkoxy group.

X may be F, Cl, Br or I.

Above A may be

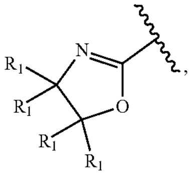,
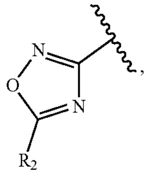,
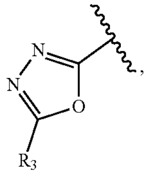,
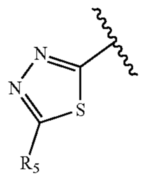
or
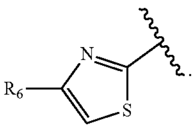.

$R_1$ to $R_3$, $R_5$, and $R_6$ may be each independently at least one substituent selected from the group consisting of a hydrogen atom, a halogen atom, a C1-C6 straight or branched chain alkyl group and a C1-C6 straight or branched chain hydroxyalkyl group. The alkyl group or the hydroxyalkyl group may be each independently unsubstituted or substituted with a halogen atom or a C1-C6 alkoxy group.

Above B may be

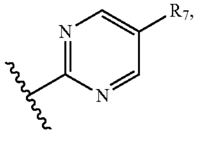
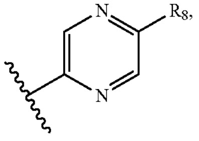
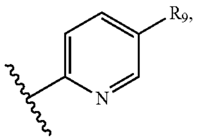
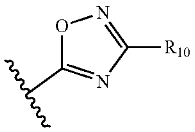
or
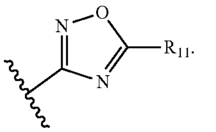

Above $R_7$ to $R_{11}$, may be each independently substituted with at least one substituent selected from the group consisting of a hydrogen atom, a halogen atom, a C1-C6 straight or branched chain alkyl group, a C1-C6 straight or branched chain hydroxyalkyl group, a C1-C6 alkoxy group and an oxadiazole group. The alkyl group, the hydroxyalkyl group, the alkoxy group or the oxadiazole group may be each independently unsubstituted or substituted with a halogen atom, a C1-C6 alkyl group or a C1-C6 alkoxy group.

X may be F.

In above Formula 1, above A may be an oxadiazole group substituted with a C1-C6 straight or branched chain alkyl group, above B may be a pyrimidine group substituted with a C1-C6 straight or branched chain alkyl group, and X may be F.

In the present embodiment, the term "halogen" may refer to fluorine, chlorine, bromine or iodine.

In one embodiment, the term "alkyl" may refer to a straight or branched chain hydrocarbon residue unless otherwise specified. An example of the C1-C6 alkyl may include methyl, ethyl, propyl, isopropyl, butyl, isobutyl, pentyl, hexyl, etc.

In one embodiment, the term "alkoxy" may include an alkyl-oxygen radical having alkyl as defined above unless otherwise specified. An example of the C1-C6 alkoxy may include methoxy, ethoxy, propoxy, butoxy, pentoxy, etc.

In one embodiment, the term "heterocycle" or "heterocyclic" may refer to a 5 to 13-membered hetero-aromatic or non-aromatic compound including 1 to 3 heteroatoms selected from the group consisting of N, O, and S unless otherwise specified.

In one embodiment, the compound represented by above Formula 1 may be at least one compound specifically selected from the group consisting of the following compounds:

2-(4-(3-(1-(5-ethylpyrimidin-2-yl)piperidin-4-yl)propoxy)-2,6-difluorophenyl)-4,5-dihydrooxazole, (R)-2-(4-(3-(1-(5-ethylpyrimidin-2-yl)piperidin-4-yl)propoxy)-2,6-difluorophenyl)-4-methyl-4,5-dihydrooxazole, (S)-2-(4-(3-(1-(5-ethylpyrimidin-2-yl)piperidin-4-yl)propoxy)-2,6-difluorophenyl)-4-methyl-4,5-dihydrooxazole, (S)-2-(4-(3-(1-(5-ethylpyrimidin-2-yl)piperidin-4-yl)propoxy)-2,6-difluorophenyl)-5-methyl-4,5-dihydrooxazole, (R)-2-(4-(3-(1-(5-ethylpyrimidin-2-yl)piperidin-4-yl)propoxy)-2,6-difluorophenyl)-5-methyl-4,5-dihydrooxazole, 2-(4-(3-(1-(5-ethylpyrimidin-2-yl)piperidin-4-yl)propoxy)-2,6-difluorophenyl)-5,5-dimethyl-4,5-dihydrooxazole, (R)-(2-(4-(3-(1-(5-ethylpyrimidin-2-yl)piperidin-4-yl)propoxy)-2,6-difluorophenyl)-4,5-dihydrooxazole-5-yl)methanol, (S)-(2-(4-(3-(1-(5-ethylpyrimidin-2-yl)piperidin-4-yl)propoxy)-2,6-difluorophenyl)-4,5-dihydrooxazole-5-yl)methanol, (R)-3-(2-(4-(3-(3,5-difluoro-4-(5-methyl-4,5-dihydrooxazole-2-yl)phenoxy)propyl)piperidin-1-yl)pyrimidin-5-yl)-5-isobutyl-1,2,4-oxadiazole, (R)-5-(4-(3-(3,5-difluoro-4-(4-methyl-4,5-dihydrooxazol-2-yl)phenoxy)propyl)piperidin-1-yl)-3-isopropyl-1,2,4-oxadiazole, (S)-5-(4-(3-(3,5-difluoro-4-(5-methyl-4,5-dihydrooxazol-2-yl)phenoxy)propyl)piperidin-1-yl)-3-isopropyl-1,2,4-oxadiazole, 5-(4-(3-(4-(5,5-dimethyl-4,5-dihydrooxazol-2-yl)-3,5-difluorophenoxy)propyl)piperidin-1-yl)-3-isopropyl-1,2,4-oxadiazole, 3-(4-(3-(1-(5-ethylpyrimidin-2-yl)piperidin-4-yl)propoxy)-2,6-difluorophenyl)-5-methyl-1,2,4-oxadiazole, 3-(4-(3-(1-(5-ethylpyrimidin-2-yl)piperidin-4-yl)propoxy)-2,6-difluorophenyl)-5-propyl-1,2,4-oxadiazole, 3-(4-(3-(1-(5-ethylpyrimidin-2-yl)piperidin-4-yl)propoxy)-2,6-difluorophenyl)-5-isopropyl-1,2,4-oxadiazole, 5-(tert-butyl)-3-(4-(3-(1-(5-ethylpyrimidin-2-yl)piperidin-4-yl)propoxy)-2,6-difluorophenyl)-1,2,4-oxadiazole, (3-(4-(3-(1-(5-ethylpyrimidin-2-yl)piperidin-4-yl)propoxy)-2,6-difluorophenyl)-1,2,4-oxadiazol-5-yl)methanol, 2-(3-(4-(3-(1-(5-ethylpyrimidin-2-yl)piperidin-4-yl)propoxy)-2,6-difluorophenyl)-1,2,4-oxadiazol-5-yl)ethan-1-ol, (S)-1-(3-(4-(3-(1-(5-ethylpyrimidin-2-yl)piperidin-4-yl)propoxy)-2,6-difluorophenyl)-1,2,4-oxadiazole-5-yl)propan-1-ol, (R)-1-(3-(4-(3-(1-(5-ethylpyrimidin-2-yl)piperidin-4-yl)propoxy)-2,6-difluorophenyl)-1,2,4-oxadiazol-5-yl)propane-2-ol, (S)-1-(3-(4-(3-(1-(5-ethylpyrimidin-2-yl)piperidin-4-yl)propoxy)-2,6-difluorophenyl)-1,2,4-oxadiazol-5-yl)propan-2-ol, 2-(3-(4-(3-(1-(5-ethylpyrimidin-2-yl)piperidin-4-yl)propoxy)-2,6-difluorophenyl)-1,2,4-oxadiazol-5-yl)-2-methylpropan-1-ol, 3-(2,6-difluoro-4-(3-(1-(5-propylpyrimidin-2-yl)piperidin-4-yl)propoxy)phenyl)-5-isopropyl-1,2,4-oxadiazole, 3-(2,6-difluoro-4-(3-(1-(5-pentylpyrimidin-2-yl)piperidin-4-yl)propoxy)phenyl)-5-isopropyl-1,2,4-oxadiazole, 3-(2,6-difluoro-4-(3-(1-(5-(trifluoromethyl)pyrimidin-2-yl)piperidin-4-yl)propoxy)phenyl)-5-isopropyl-1,2,4-oxadiazole, 3-(2,6-difluoro-4-(3-(1-(5-methoxypyrimidin-2-yl)piperidin-4-yl)propoxy)phenyl)-5-isopropyl-1,2,4-oxadiazole, 3-(2,6-difluoro-4-(3-(1-(5-isopropoxypyrimidin-2-yl)piperidin-4-yl)propoxy)phenyl)-5-isopropyl-1,2,4-oxadiazole,
3-(4-(3-(1-(5-chloropyrimidin-2-yl)piperidin-4-yl)propoxy)-2,6-difluorophenyl)-5-isopropyl-1,2,4-oxadiazole,
3-(4-(3-(1-(5-bromopyrimidin-2-yl)piperidin-4-yl)propoxy)-2,6-difluorophenyl)-5-isopropyl-1,2,4-oxadiazole,
3-(2,6-difluoro-4-(3-(1-(5-(5-isobutyl-1,2,4-oxadiazol-3-yl)pyrimidin-2-yl)piperidin-4-yl)propoxy)phenyl)-5-methyl-1,2,4-oxadiazole,
3-(2,6-difluoro-4-(3-(1-(5-(5-isobutyl-1,2,4-oxadiazol-3-yl)pyrimidin-2-yl)piperidin-4-yl)propoxy)phenyl)-5-ethyl-1,2,4-oxadiazole,
3-(2,6-difluoro-4-(3-(1-(5-(5-isobutyl-1,2,4-oxadiazol-3-yl)pyrimidin-2-yl)piperidin-4-yl)propoxy)phenyl)-5-isopropyl-1,2,4-oxadiazole,
5-(sec-butyl)-3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazole,
3-(2,6-difluoro-4-(3-(1-(5-(5-isobutyl-1,2,4-oxadiazol-3-yl)pyrimidin-2-yl)piperidin-4-yl)propoxy)phenyl)-5-(methoxymethyl)-1,2,4-oxadiazole,
(S)-1-(3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazol-5-yl)propan-1-ol,
2-(3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazol-5-yl)-2-methylpropan-1-ol,
3-(4-(3-(1-(5-chloropyrazin-2-yl)piperidin-4-yl)propoxy)-2,6-difluorophenyl)-5-isopropyl-1,2,4-oxadiazole,
3-(2,6-difluoro-4-(3-(1-(5-(trifluoromethyl)pyridin-2-yl)piperidin-4-yl)propoxy)phenyl)-5-isopropyl-1,2,4-oxadiazole,
3-(2,6-difluoro-4-(3-(1-(3-isopropyl-1,2,4-oxadiazol-5-yl)piperidin-4-yl)propoxy)phenyl)-5-methyl-1,2,4-oxadiazole,
3-(2,6-difluoro-4-(3-(1-(3-isopropyl-1,2,4-oxadiazol-5-yl)piperidin-4-yl)propoxy)phenyl)-5-isopropyl-1,2,4-oxadiazole,
(3-(2,6-difluoro-4-(3-(1-(3-isopropyl-1,2,4-oxadiazol-5-yl)piperidin-4-yl)propoxy)phenyl)-1,2,4-oxadiazol-5-yl)methanol,
2-(4-(3-(1-(5-ethylpyrimidin-2-yl)piperidin-4-yl)propoxy)-2,6-difluorophenyl)-5-methyl-1,3,4-oxadiazole,
2-ethyl-5-(4-(3-(1-(5-ethylpyrimidin-2-yl)piperidin-4-yl)propoxy)-2,6-difluorophenyl)-1,3,4-oxadiazole,
2-(4-(3-(1-(5-ethylpyrimidin-2-yl)piperidin-4-yl)propoxy)-2,6-difluorophenyl)-5-isopropyl-1,3,4-oxadiazole,
5-(4-(3-(1-(5-ethylpyrimidin-2-yl)piperidin-4-yl)propoxy)-2,6-difluorophenyl)-N-isopropyl-1,3,4-oxadiazol-2-amine,
2-(2,6-difluoro-4-(3-(1-(5-(trifluoromethyl)pyrimidin-2-yl)piperidin-4-yl)propoxy)phenyl)-5-methyl-1,3,4-oxadiazole,
2-(2,6-difluoro-4-(3-(1-(5-(trifluoromethyl)pyrimidin-2-yl)piperidin-4-yl)propoxy)phenyl)-5-ethyl-1,3,4-oxadiazole,
2-(2,6-difluoro-4-(3-(1-(5-(trifluoromethyl)pyrimidin-2-yl)piperidin-4-yl)propoxy)phenyl)-5-isopropyl-1,3,4-oxadiazole,
2-(4-(3-(1-(5-chloropyrazin-2-yl)piperidin-4-yl)propoxy)-2,6-difluorophenyl)-5-methyl-1,3,4-oxadiazole,
2-(4-(3-(1-(5-chloropyrazin-2-yl)piperidin-4-yl)propoxy)-2,6-difluorophenyl)-5-ethyl-1,3,4-oxadiazole,
2-(4-(3-(1-(5-chloropyrazin-2-yl)piperidin-4-yl)propoxy)-2,6-difluorophenyl)-5-isopropyl-1,3,4-oxadiazole,
5-(4-(3-(3,5-difluoro-4-(5-methyl-1,3,4-oxadiazol-2-yl)phenoxy)propyl)piperidin-1-yl)-3-propyl-1,2,4-oxadiazole,
5-(4-(3-(3,5-difluoro-4-(5-ethyl-1,3,4-oxadiazol-2-yl)phenoxy)propyl)piperidin-1-yl)-3-propyl-1,2,4-oxadiazole,
5-(4-(3-(3,5-difluoro-4-(5-isopropyl-1,3,4-oxadiazol-2-yl)phenoxy)propyl)piperidin-1-yl)-3-propyl-1,2,4-oxadiazole,
5-(4-(3-(3,5-difluoro-4-(5-methyl-1,3,4-oxadiazol-2-yl)phenoxy)propyl)piperidin-1-yl)-3-isopropyl-1,2,4-oxadiazole,
5-(4-(3-(4-(5-ethyl-1,3,4-oxadiazol-2-yl)-3,5-difluorophenoxy)propyl)piperidin-1-yl)-3-isopropyl-1,2,4-oxadiazole,
5-(4-(3-(3,5-difluoro-4-(5-isopropyl-1,3,4-oxadiazol-2-yl)phenoxy)propyl)piperidin-1-yl)-3-isopropyl-1,2,4-oxadiazole,
5-(4-(3-(3,5-difluoro-4-(5-methyl-1,3,4-oxadiazol-2-yl)phenoxy)propyl)piperidin-1-yl)-3-(2,2,2-trifluoroethyl)-1,2,4-oxadiazole,
3-(4-(3-(3,5-difluoro-4-(5-isopropyl-1,3,4-oxadiazol-2-yl)phenoxy)propyl)piperidin-1-yl)-5-isopropyl-1,2,4-oxadiazole,
2-(4-(3-(1-(5-ethylpyrimidin-2-yl)piperidin-4-yl)propoxy)-2,6-difluorophenyl)-5-isopropyl-1,3,4-thiadiazole,
2-(2,6-difluoro-4-(3-(1-(5-propylpyrimidin-2-yl)piperidin-4-yl)propoxy)phenyl)-5-isopropyl-1,3,4-thiadiazole,
2-(2,6-difluoro-4-(3-(1-(5-pentylpyrimidin-2-yl)piperidin-4-yl)propoxy)phenyl)-5-isopropyl-1,3,4-thiadiazole,
2-(2,6-difluoro-4-(3-(1-(5-fluoropyrimidin-2-yl)piperidin-4-yl)propoxy)phenyl)-5-isopropyl-1,3,4-thiadiazole,
2-(2,6-difluoro-4-(3-(1-(5-(trifluoromethyl)pyrimidin-2-yl)piperidin-4-yl)propoxy)phenyl)-5-isopropyl-1,3,4-thiadiazole,
2-(2,6-difluoro-4-(3-(1-(5-(trifluoromethyl)pyridin-2-yl)piperidin-4-yl)propoxy)phenyl)-5-isopropyl-1,3,4-thiadiazole, and
4-ethyl-2-(4-(3-(1-(5-ethylpyrimidin-2-yl)piperidin-4-yl)propoxy)-2,6-difluorophenyl)thiazole.

In one embodiment, the compound represented by above Formula 1 may be 3-(4-(3-(1-(5-ethylpyrimidin-2-yl)piperidin-4-yl)propoxy)-2,6-difluorophenyl)-5-isopropyl-1,2,4-oxadiazole.

The pharmaceutical composition of one embodiment may include a compound represented by above Formula 1; and any one selected from the PPAR agonist, the DPPIV inhibitor, the ACC inhibitor, the FXR agonist and the CCR2/5 dual antagonist.

The PPAR agonist may be at least one of pioglitazone, lobeglitazone, elafibranor, lanifibranor and saroglitazar. The DPPIV inhibitor may be at least one of sitagliptin, vildagliptin, saxagliptin, linagliptin, gemigliptin, anagliptin, teneligliptin, alogliptin, trelagliptin, omarigliptin, evogliptin, gosogliptin and dutogliptin. The ACC inhibitor may be firsocostat. The FXR agonist may be at least one of obeticholic acid, tropifexor and GW4064 (3-(2,6-dichlorophenyl)-4-(3'-carboxy-2-chlorostilben-4-yl)oxymethyl-5-isopropylisoxazole). The CCR 2/5 dual antagonist may be cenicriviroc.

For example, the pharmaceutical composition may include a compound represented by above Formula 1 and the PPAR agonist, the DPPIV inhibitor, the ACC inhibitor, the FXR agonist or the CCR2/5 dual antagonist. The pharmaceutical composition may include the 3-(4-(3-(1-(5-ethylpyrimidin-2-yl)piperidin-4-yl)propoxy)-2,6-difluorophenyl)-

5-isopropyl-1,2,4-oxadiazole and the PPAR agonist. The pharmaceutical composition may include the 3-(4-(3-(1-(5-ethylpyrimidin-2-yl)piperidin-4-yl)propoxy)-2,6-difluorophenyl)-5-isopropyl-1,2,4-oxadiazole and the DPPIV inhibitor. The pharmaceutical composition may include the 3-(4-(3-(1-(5-ethylpyrimidin-2-yl)piperidin-4-yl)propoxy)-2,6-difluorophenyl)-5-isopropyl-1,2,4-oxadiazole and the ACC inhibitor. The pharmaceutical composition may include the 3-(4-(3-(1-(5-ethylpyrimidin-2-yl)piperidin-4-yl)propoxy)-2,6-difluorophenyl)-5-isopropyl-1,2,4-oxadiazole and the FXR agonist. The pharmaceutical composition may include the 3-(4-(3-(1-(5-ethylpyrimidin-2-yl)piperidin-4-yl)propoxy)-2,6-difluorophenyl)-5-isopropyl-1,2,4-oxadiazole and the CCR 2/5 dual agonist.

The PPAR agonist may be elafibranor. The DPPIV inhibitor may be at least one of evogliptin and sitagliptin. The ACC inhibitor may be firsocostat. The FXR agonist may be obeticholic acid. The CCR 2/5 dual antagonist may be cenicriviroc.

The pharmaceutical composition may include the 3-(4-(3-(1-(5-ethylpyrimidin-2-yl)piperidin-4-yl)propoxy)-2,6-difluorophenyl)-5-isopropyl-1,2,4-oxadiazole and the elafibranor, evogliptin, sitagliptin, firsocostat, obeticholic acid or cenicriviroc.

The nonalcoholic fatty liver disease may be selected from the group consisting of nonalcoholic fatty liver, nonalcoholic steatohepatitis, liver fibrosis and cirrhosis.

The pharmaceutical composition may be a pharmaceutical composition for preventing or treating nonalcoholic fatty liver disease by inhibiting deposition of triglycerides in liver tissues.

The pharmaceutical composition may be a pharmaceutical composition for preventing or treating nonalcoholic fatty liver disease by inhibiting occurrence of inflammation in liver tissues.

The pharmaceutical composition may be a pharmaceutical composition for preventing or treating nonalcoholic fatty liver disease by inhibiting fibrosis of liver tissues.

When it is described in the present specification that the pharmaceutical composition includes A and B, the pharmaceutical composition may be construed to mean a composition including A and B; a combination including A and B, respectively, as a separate preparation; or a composition including the combination. Thus, in the present invention, the composition may be used interchangeably with the combination.

The pharmaceutical composition may be one which includes a compound represented by Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist, respectively, as a separate preparation or includes all in the form of a combination preparation.

The pharmaceutical composition may be a combination of separate preparations, or a combination preparation.

The pharmaceutical composition may include a first compartment containing a first active ingredient, and a second compartment containing a second active ingredient.

The first active ingredient may be a compound represented by Formula 1, pharmaceutically acceptable salts thereof, optical isomers thereof, hydrates thereof, solvates thereof or mixtures thereof. The second active ingredient may include at least one selected from a PPAR agonist, a DPPIV inhibitor, an ACC inhibitor, a FXR agonist and a CCR2/5 dual antagonist.

According to embodiments of the present invention, in the pharmaceutical composition, the first compartment containing the first active ingredient and the second compartment containing the second active ingredient may be co-administered, and thus the pharmaceutical composition may be a composition for co-administration. Specifically, the pharmaceutical composition may be a combination in which two ingredients are formulated into separate unit dosage forms. In this case, the first active ingredient and the second active ingredient may be administered in combination as separate dosage forms.

In one specific embodiment of the present invention, in a C57BL/6J mouse model in which nonalcoholic fatty liver disease was induced according to the supply of special feed, it was found that the pharmaceutical composition of one embodiment is effective in the treatment and prevention of nonalcoholic liver disease through histological examination, confirmation of concentration of inflammation and fibrosis-related proteins, blood AST and ALT measurement experiments, and the like.

More specifically, when administering the pharmaceutical composition according to one embodiment, it is confirmed that a nonalcoholic fatty liver disease (NAFLD) activity score is lowered, a relative proportion of lipid droplets per unit area is decreased, an infiltration of inflammatory cells in liver tissues is reduced, a fibrosis of liver tissues is inhibited, and an effect of ameliorating blood inflammatory and fibrotic biomarkers are increased, and a concentration of AST and ALT in blood is decreased, compared to when co-administering a compound represented by Formula 1, pharmaceutically acceptable salts thereof, optical isomers thereof, hydrates thereof, solvates thereof or mixtures thereof as a GPR119 agonist; or a PPAR agonist, a DPPIV inhibitor, an ACC inhibitor, a FXR agonist or a CCR2/5 dual antagonist, respectively.

In the present invention, a non-limiting example of the pharmaceutically acceptable salts of the compound represented by above formula 1 may include inorganic acid salts such as hydrochloric acid, bromic acid, phosphoric acid or sulfuric acid; organic carboxylic acid salts such as acetic acid, trifluoroacetic acid, citric acid, maleic acid, oxalic acid, succinic acid, benzoic acid, tartaric acid, fumaric acid, mandelic acid, ascorbic acid or malic acid, or sulfonic acid salts such as methanesulfonic acid or para-toluenesulfonic acid; alkali metal salts such as sodium, potassium or lithium; various acid salts known to be capable of forming other pharmaceutically acceptable salts; or the like.

The pharmaceutical composition for preventing or treating nonalcoholic fatty liver disease according to one embodiment may be used in the form of a general pharmaceutical preparation. The pharmaceutical preparation may be administered in several oral and parenteral dosage forms upon administration, and the dosage form may be variously determined according to a method of use.

If the pharmaceutical composition of one embodiment is formulated into several oral and parenteral dosage forms, it may be possible to use the generally used excipients such as fillers, diluents, extenders, binders, humectants, disintegrants, surfactants, etc.

A solid preparation for oral administration may include tablets, pills, powders, granules, capsules, etc., and these solid preparations may be prepared by mixing at least one excipient, for example, starch, calcium carbonate, sucrose, lactose, gelatin or the like in the pharmaceutical composition. In addition, lubricants such as magnesium stearate, tale, etc., may be used in addition to simple excipients.

Furthermore, a liquid preparation for oral administration may include suspending agents, liquids for internal use, emulsions, syrups, etc., but may also include several excipients, for example, humectants, sweetening agents, flavoring agents, preservatives, etc. in addition to water and liquid paraffin, which are the frequently used simple diluents.

A preparation for parenteral administration may include sterile aqueous solutions, non-aqueous solvents, suspensions, emulsions, lyophilized preparations and suppositories. The non-aqueous solvent and the suspending agent used herein may include propylene glycol, polyethylene glycol, vegetable oil like olive oil, injectable ester like ethyl oleate, etc. A base of the suppository used herein may include witepsol, macrogol, tween 61, cacao butter, laurinum, glycerogelatin, etc.

In addition, the pharmaceutical composition for preventing or treating nonalcoholic fatty liver disease according to the present invention may represent an effective amount in an administration range of about 1 to about 1,000 mg. An administered amount or an intake amount may be administered with a variety of administered doses and methods, such as once a day or several times a day by dividing the composition depending on a subject's body weight, age, gender, health condition, diet, administration time, administration method, excretion rate, and severity of the disease.

In the present invention, nonalcoholic fatty liver disease (NAFLD) may include both primary and secondary nonalcoholic fatty liver diseases. Specifically, in the present invention, nonalcoholic fatty liver disease (NAFLD) may include simple steatosis, nonalcoholic steatohepatitis (NASH), and liver fibrosis and liver cirrhosis caused by the progression of these diseases, but is not limited to.

The pharmaceutical composition of one embodiment may include a compound represented by Formula 1 or an active ingredient having a similar function thereto; and at least one selected from a PPAR agonist, a DPPIV inhibitor, an ACC inhibitor, a FXR agonist and a CCR2/5 dual antagonist.

The present invention may also provide a method for preventing or treating nonalcoholic fatty liver disease, including administering into a subject in need of treatment a therapeutically effective amount of a pharmaceutical composition including a compound represented by Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist.

In the present invention, the term "subject in need of treatment" may mean mammals including humans, and the term "administration" may refer to providing a predetermined material to subjects by any appropriate method. The term "therapeutically effective amount" may refer to an amount of an active ingredient or a pharmaceutical composition which induces animals or humans to show the biological or medical responses considered by investigators, veterinarians, doctors or other clinicians, and may include an amount thereof for inducing a relief of symptoms of diseases or disorders to be treated. It is apparent to those skilled in the art that a therapeutically effective dosage and the number of administration for active ingredient of the present invention may vary depending on a desired effect.

In one embodiment, the term, a route of administration of the pharmaceutical composition of the present invention may be administered through any general route as long as it can reach a target tissue.

Administration may be performed orally, intraperitoneally, intravenously, intramuscularly, subcutaneously, endothelially, intranasally, intrapulmonarily, rectally, intracavitarily, intraperitoneally and intrathecally, but is not limited thereto.

The pharmaceutical composition of one embodiment may be administered once a day or at least twice a day at a certain interval of time.

The pharmaceutical composition of one embodiment may be used alone or in combination with a surgery, endocrinotherapy, drug treatment and methods of using a biologic response modifier, in order to prevent and treat nonalcoholic fatty liver disease.

One embodiment may also provide a food composition for preventing or ameliorating nonalcoholic fatty liver disease, including a compound represented by above Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist as an active ingredient.

In one embodiment, the term "amelioration" may refer to all the acts, in which a disease gets better or takes a favorable turn by administering the composition.

In one embodiment, the term "food" may refer to meats, sausages, breads, chocolates, candies, snacks, confectioneries, pizzas, instant noodles, other noodles, chewing gums, dairy products including ice creams, various types of soup, beverages, teas, health drinks, alcohol beverages, vitamin complexes, health functional foods, health foods, health supplement foods and the like, and include all the foods in a conventional sense.

The term "health functional food" may be the same term as food for special health use (FoSHU), and refer to the food having a high medical and medicinal effect, which is processed to efficiently show a biomodulation function in addition to supplying nutrients. In this case, the "function (ality)" may refer to controlling nutrients or obtaining a beneficial effect on health uses such as a physiological action, etc., with regard to the structure and function of the human body.

The "health food" may refer to food having an effect of actively maintaining or enhancing health compared to general food, and the "health supplement food" may refer to food for a health supplement purpose. In some cases, the terms of health functional food, health food, and health supplement food may be used interchangeably.

The food of the present invention may be prepared by a method conventionally used in the art, and raw materials and ingredients conventionally added in the art may be added to prepare the food during the preparation. Specifically, proteins, carbohydrates, fats, nutrients, seasoning agents, and flavoring agents may be included, and an example of the carbohydrates may include glucose, fructose, maltose, sucrose, oligosaccharide, dextrin, cyclodextrin, xylitol, sorbitol, erythrol, saccharin or synthetic flavoring agents, but is not limited thereto. The food composition of the present invention may be prepared into various dosage forms without limitation, as long as the dosage form is recognized as food.

The present invention may also provide a method for preventing or ameliorating nonalcoholic fatty liver disease, including administering into a subject in need of amelioration a food composition including a compound represented by above Formula 1, pharmaceutically acceptable salts thereof, optical isomers thereof, hydrates thereof, solvates thereof, or mixtures thereof; and at least one selected from a PPAR agonist, a DPPIV inhibitor, an ACC inhibitor, a FXR agonist and a CCR2/5 dual antagonist as an active ingredient.

The present invention may also provide a feed composition for preventing or ameliorating nonalcoholic fatty liver disease, including a compound represented by above formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist as an active ingredient.

In the present invention, the term "feed" may refer to any natural or artificial diet, one meal, etc., or an ingredient of the one meal, which is to be consumed or digested by livestock or appropriate thereto. The feed may include feed additives or auxiliary feeds.

The kind of the feed is not particularly limited, and the feed conventionally used in the art may be used. A non-limiting example of the feed may include vegetable feeds such as grains, root fruits, food processing by-products, algae, fibers, pharmaceutical by-products, oils and fats, starches, oil meals, grain by-products or the like; animal feeds such as proteins, inorganic matters, oils and fats, minerals, single-cell proteins, zooplanktons, foods or the like. The feed may be used alone or by mixing at least two thereof.

The present invention may also provide a use of the pharmaceutical composition including a compound represented by above Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist as an active ingredient for preventing or treating nonalcoholic fatty liver disease.

The present invention may also provide a use of the pharmaceutical composition including a compound represented by above Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist as an active ingredient, in the manufacture of a medicament for preventing or treating nonalcoholic fatty liver disease.

The present invention may also provide a method for preventing or treating nonalcoholic steatohepatitis, including administering into a subject in need of treatment a therapeutically effective amount of a pharmaceutical composition including a compound represented by above Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist.

The present invention may also provide a combination of a compound represented by above Formula 1, pharmaceutically acceptable salts thereof, optical isomers thereof, hydrates thereof, solvates thereof or mixtures thereof; and at least one selected from a PPAR agonist, a DPPIV inhibitor, an ACC inhibitor, a FXR agonist and a CCR2/5 dual antagonist.

The present invention may also provide a pharmaceutical composition for preventing or treating nonalcoholic steatohepatitis, including a compound represented by above Formula 1, pharmaceutically acceptable salts thereof, optical isomers thereof, hydrates thereof, solvates thereof or mixtures thereof in combination with at least one selected from a PPAR agonist, a DPPIV inhibitor, an ACC inhibitor, a FXR agonist and a CCR2/5 dual antagonist.

In the therapeutic method, the food composition, the amelioration method, the feed composition, the use and the combination thereof, the compound represented by above Formula 1 may be specifically 3-(4-(3-(1-(5-ethylpyrimidin-2-yl)piperidin-4-yl)propoxy)-2,6-difluorophenyl)-5-isopropyl-1,2,4-oxadiazole.

Matters mentioned in each of the pharmaceutical composition, the therapeutic method, the food composition, the amelioration method, the feed composition, the use and combinations thereof according to an embodiment of the present invention are applied the same to each of embodiments, if not contradictory to each other.

Advantageous Effects

A pharmaceutical composition according to the present invention shows an excellent effect of ameliorating lipid metabolism, reducing fat accumulation in liver tissues, and preventing histological damage caused by inflammation and fibrosis of liver tissues, and thus can be effectively used for preventing or treating nonalcoholic fatty liver disease.

MODE FOR INVENTION

Figure 1:
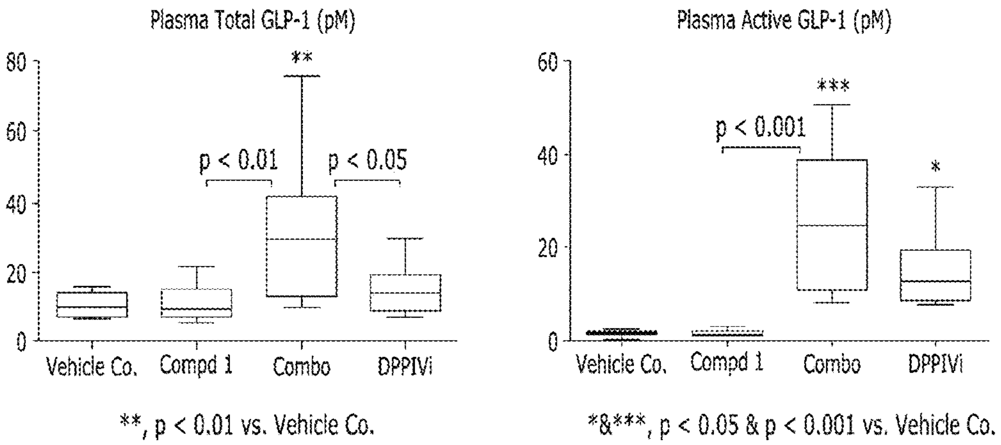
FIG. 1 shows an effect of co-administration on a change in concentration of total GLP-1 and active GLP-1 in postprandial plasma after a single oral administration of a drug to normal mice.

The features and advantages of the present invention as well as methods for achieving them will be apparent with reference to exemplary embodiments described in detail hereinafter. However, the present invention is not limited to the exemplary embodiments disclosed hereinafter, but will be implemented in various different forms. Hereinafter, the following exemplary embodiments will be suggested for better understanding of the present invention and are provided only for the purpose of completely illustrating the scope of the present invention to those skilled in the art, and thus the present invention will be defined only by the scope of the claims thereto.

Nonalcoholic steatohepatitis is not a disease caused by a single factor, and thus it may be difficult to expect an excellent therapeutic effect with a single drug. Accordingly, the pharmaceutical composition according to one embodiment of the present invention, including a plurality of active ingredients, may improve an effect of preventing or treating nonalcoholic steatohepatitis according to administration in combination with complementary drugs of various mechanisms.

Drugs, which are under current development as therapeutic agents for nonalcoholic steatohepatitis, are roughly classified into i) drugs for reducing fat accumulation in liver tissues through metabolic improvement, ii) drugs for reducing oxidative stress in liver tissues or inhibiting inflammatory responses through direct control thereof, iii) drugs for inhibiting apoptosis of hepatocytes, and iv) drugs for inhibiting accumulation of extracellular fibrotic proteins.

In particular, metabolic diseases such as obesity and diabetes have a high morbidity rate and have etiological characteristics in which a metabolic imbalance causes fat accumulation in liver tissues, and thus diabetic drugs with various mechanisms previously developed for the purpose of improving metabolism have been confirmed to be effective in animal models with nonalcoholic steatohepatitis or have been in clinical exploratory study.

The pharmaceutical composition according to one embodiment of the present invention may include a GPR119 agonist and at least one selected from a peroxisome proliferator-activated receptor (PPAR) agonist, a dipeptidyl peptidase IV (DPPIV) inhibitor, an acetyl coenzyme A carboxylase (ACC) inhibitor, farnesoid X receptor (FXR) agonist and C—C chemokine receptor 2/5 (CCR2/5) dual antagonist. Thus, the pharmaceutical composition may exhibit an excellent effect of treating or preventing nonalcoholic steatohepatitis by complementary effects of the active ingredients described above. More specifically, the pharmaceutical composition of one embodiment may exhibit a synergistic effect on the treatment or prevention of nonalcoholic steatohepatitis compared to the case of individually administering each of the above-described active ingredients.

In the present specification, "at least one" may be construed to indicate all combinations derived from a plurality of configurations. For example, "at least one of A, B and C" may be construed to include "A, B or C", "two selected from A, B and C" and all combinations derived from "A, B and C."

GPR119 may be one of G protein-coupled receptors (GPCRs) to which Gs is coupled to activate signaling through cAMP. GPR119 has a high expression level in pancreatic beta cells and L cells of small intestines, is also present in the liver, and serves as a regulator of fatty acid biosynthesis in the liver. In addition, when GP119 is activated, it is possible to control all of fatty liver, inflammation, and fibrosis in nonalcoholic steatohepatitis by inhibiting the differentiation and activation of inflammatory cells and the activation of hepatic stellate cells.

Mechanistically, when GPR119 in small intestines is activated by fatty acid derivatives derived from ingested food, GPR119 may increase the secretion of glucagon-like peptide-1 (GLP-1). Secreted GLP-1 is inactivated by an enzyme called dipeptidyl peptidase IV (DPPIV) within minutes in the blood.

GLP-1 may have a pharmacological effect on metabolic improvement, and GLP-1-like peptide may ameliorate fatty liver in patients with nonalcoholic steatohepatitis in the clinic.

Referring to the above-described mechanism, when administering a GPR119 agonist (e.g., the compound represented by Formula 1 described above) in combination with a DPPIV inhibitor developed as a hypoglycemic agent, the duration of biological activity of active GLP-1 in the blood may be prolonged. Accordingly, it may be possible to show an effect of the GPR119 agonist on treating or preventing nonalcoholic steatohepatitis and a pharmacological effect of GLP-1 of ameliorating the metabolism at the same time.

In other words, the pharmaceutical composition of one embodiment, including both the GPR119 agonist and the DPPIV inhibitor, may complement effects of GLP-1 on ameliorating metabolism in addition to medicinal effects of the GPR119 agonist per se on ameliorating nonalcoholic steatohepatitis. Thus, the pharmaceutical composition may be regarded to show a synergistic effect of treating and preventing nonalcoholic steatohepatitis.

The GPR119 agonist may be a GPR119 ligand, and more specifically may be a compound represented by Formula 1 described above.

The pharmaceutical composition according to one embodiment may include various combinations of active ingredients in addition to the combination of the GPR119 agonist and the DDPIV inhibitor. For example, the pharmaceutical composition according to one embodiment may include the above-described PPAR agonist or ACC inhibitor as ingredients, which increase effectiveness for treating or preventing nonalcoholic steatohepatitis by enhancing a metabolic improvement effect in combination with the GPR119 agonist, in addition to the DPPIV inhibitor which is an ingredient exhibiting the effect of improving metabolism together with the GPR119 agonist. Alternatively, the pharmaceutical composition may include a FXR agonist or a CCR 2/5 dual antagonist, which may further ameliorate inflammation and fibrosis in patients with nonalcoholic steatohepatitis in combination with the GPR119 agonist.

More specifically, the PPAR agonist may be at least one of pioglitazone, lobeglitazone, elafibranor, lanifibranor and saroglitazar; the DPPIV Inhibitor may be at least one of sitagliptin, vildagliptin, saxagliptin, linagliptin, gemigliptin, anagliptin, teneligliptin, alogliptin, trelagliptin, omarigliptin, evogliptin, gosogliptin and dutogliptin; and the ACC inhibitor may be firsocostat. The FXR agonist may be at least one of obeticholic acid, tropifexor and GW4064 (3-(2,6-dichlorophenyl)-4-(3'-carboxy-2-chlorostilben-4-yl) oxymethyl-5-isopropylisoxazole). The CCR 2/5 dual antagonist may be cenicriviroc.

The pharmaceutical composition of one embodiment may include the GPR119 agonist; and at least one of the PPAR agonist, the DPPIV inhibitor, the ACC inhibitor, the FXR agonist and the CCR2/5 dual antagonist described above.

The pharmaceutical composition of one embodiment may include the compound represented by Formula 1 described above; and at least one of the PPAR agonist, the DPPIV inhibitor, the ACC inhibitor, the FXR agonist and the CCR2/5 dual antagonist.

The pharmaceutical composition of one embodiment may include 3-(4-(3-(1-(5-ethylpyrimidin-2-yl)piperidin-4-yl) propoxy)-2,6-difluorophenyl)-5-isopropyl-1,2,4-oxadiazole; and at least one of pioglitazone, lobeglitazone, elafibranor, lanifibranor, saroglitazar, sitagliptin, vildagliptin, saxagliptin, linagliptin, gemigliptin, anagliptin, teneligliptin, alogliptin, trelagliptin, omarigliptin, evogliptin, gosogliptin and dutogliptin, firsocostat, obeticholic acid, tropifexor, GW4064, and cenicriviroc.

The pharmaceutical composition of one embodiment may include a combination of ingredients. Thus, the administration of the pharmaceutical composition of one embodiment may exhibit an excellent effect of treating or preventing nonalcoholic steatohepatitis compared to the case in which individual ingredients are administered alone.

Hereinafter, the pharmaceutical composition according to one embodiment of the present invention will be described in detail with reference to Examples and Comparative Examples.

<Example 1> Confirmation of Combination Efficacy of GPR119 Ligand and Drugs of Other Mechanisms in Mouse Model with Induced Steatohepatitis Due to Supply of Special Feed In order to confirm an effect of the pharmaceutical composition according to one embodiment of the present invention on treating nonalcoholic fatty liver disease, a following experiment was performed.

Confirmation of Mechanism of Action in Normal Mice

Seven-weeks-old male ICR mice were orally administered once with 3-(4-(3-(1-(5-ethylpyrimidin-2-yl)piperidin-4-yl)propoxy)-2,6-difluorophenyl)-5-isopropyl-1,2,4-oxadiazole (hereinafter, referred to as "compound 1") in the compound represented by Formula 1 and sitagliptin as a DPPIV inhibitor at a dose of 3 mg/kg and 10 mg/kg, respectively, alone or in combination. Glucose solution was orally loaded 30 minutes after administration. After oral glucose loading, blood was collected at a time point of 10 minutes and a total concentration of GLP-1 (ALPCO, 43-GPTHU-E01) and a concentration of active GLP-1 in plasma (ALPCO, 43-GP1HU-E01) were quantified by using an ELISA kit and the results thereof are shown in FIG. 1.

As confirmed in FIG. 1, when the GPR119 agonist and the DPPIV inhibitor were used in combination, the total concentration of GLP-1 and the peak concentration of active form in plasma were increased compared to when compound 1 was administered alone. This means that when drugs of both mechanisms are used in combination, a GLP-1 secretion in small intestines is increased and a biological half-life of GLP-1 in the blood is prolonged.

Preparation of Mouse Model with Nonalcoholic Steatohepatitis

A six-weeks-old male C57BL/6J mouse was fed with a special feed of high fat, high fructose, and high cholesterol (Research Diet, D09100301) for at least 27 weeks, and thus was induced to develop nonalcoholic steatohepatitis. After that, compound 1 was administered alone or in combination so that a daily dose reached 100 mg/kg/day. As the DPPIV inhibitor, evogliptin at 200 mg/kg/day or sitagliptin at 150 mg/kg/day was administered alone or in combination. As the PPAR agonist, elafibranor was administered alone or in combination so as to reach 30 mg/kg/day. As a method of administration alone or in combination, the above-described compound 1, DPPIV inhibitor, and/or PPAR agonist were prepared as a drug-diet admixture and supplied for 8 to 12 weeks.

Histological Examination

Figure 2:
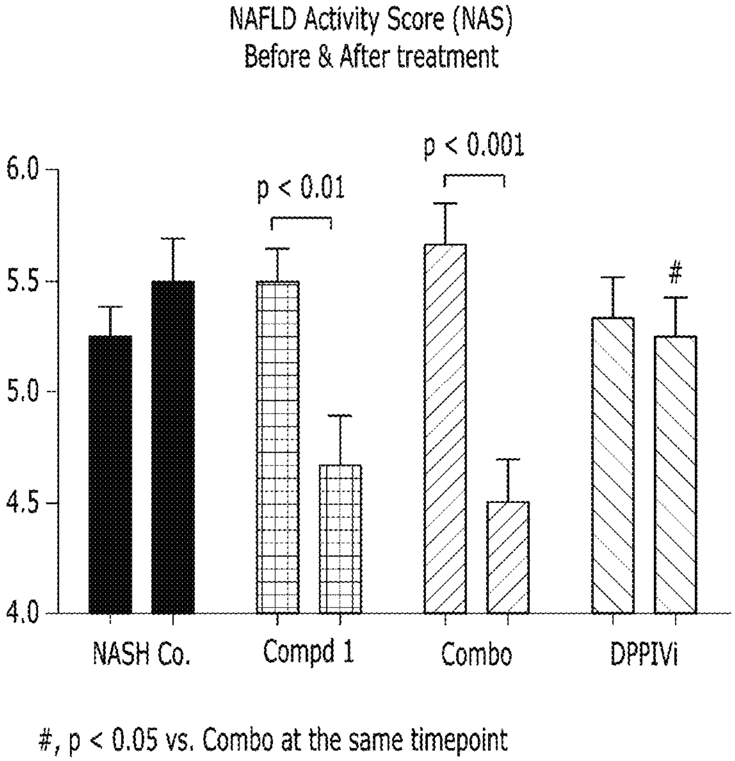
FIG. 2 shows an effect of administration in combination with a DPPIV inhibitor by comparing NAFLD activity scores before and after multiple-dose administration of a drug to mice with induced nonalcoholic steatohepatitis.
Figure 3:
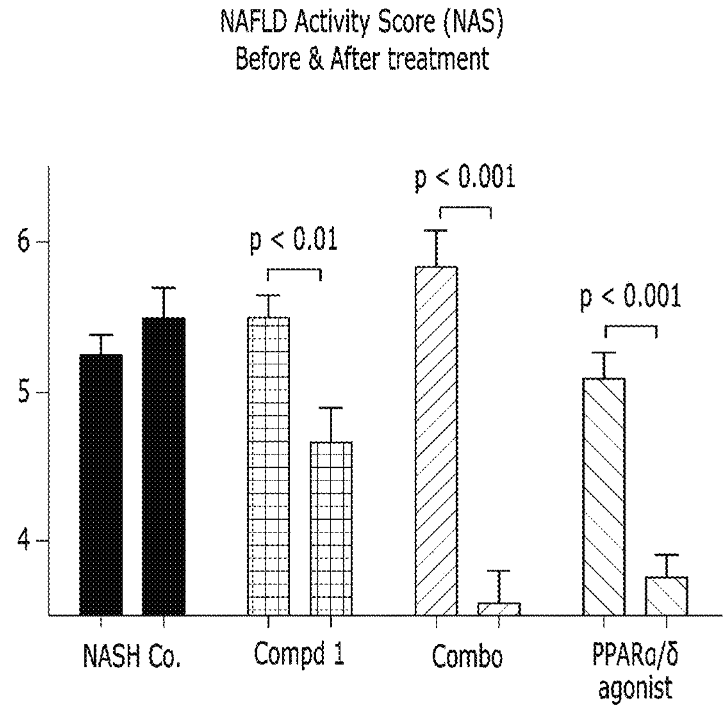
FIG. 3 shows an effect of administration in combination with a PPARα/δ agonist by comparing NAFLD activity scores before and after multiple-dose administration of a drug to mice with induced nonalcoholic steatohepatitis.

For a histological examination, liver tissues were isolated through biopsy and autopsy from the mouse model with induced nonalcoholic steatohepatitis prepared above before and after drug administration and were fixed in 10% formalin so as to prepare a paraffin block and obtain a 2 μm thick tissue section. After that, hematoxylin and eosin (HE) stain was performed by using an automatic stainer (Autostainer XL, Leica) in order to confirm an infiltration of inflammatory cells. A ratio of lipid droplets deposited in the stained liver tissues, a degree of infiltration of inflammatory cells and a degree of cell necrosis were expressed as NAFLD activity scores (NAS), and the results thereof are shown in FIGS. 2 and 3.

Figure 4:
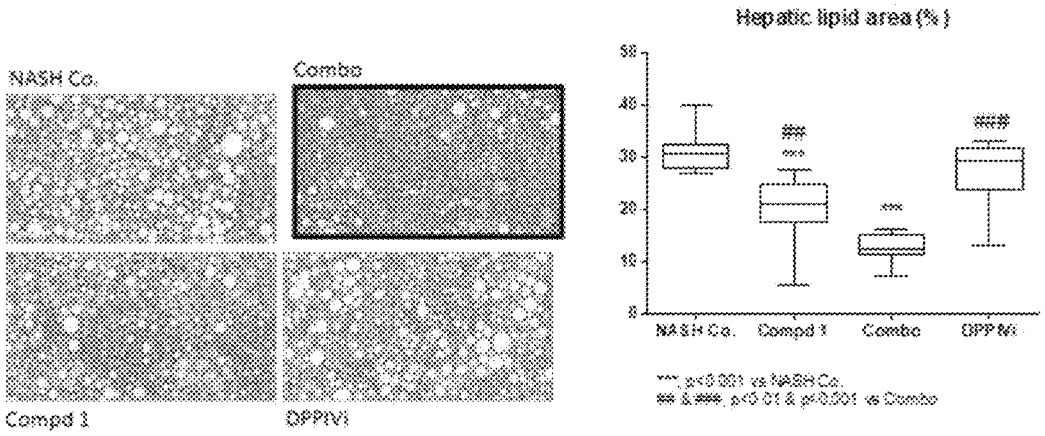
FIG. 4 shows an efficacy of administration in combination with a DPPIV inhibitor by quantifying a relative proportion of lipid droplets in liver tissues after multiple-dose administration of a drug to mice with induced nonalcoholic steatohepatitis.
Figure 5:
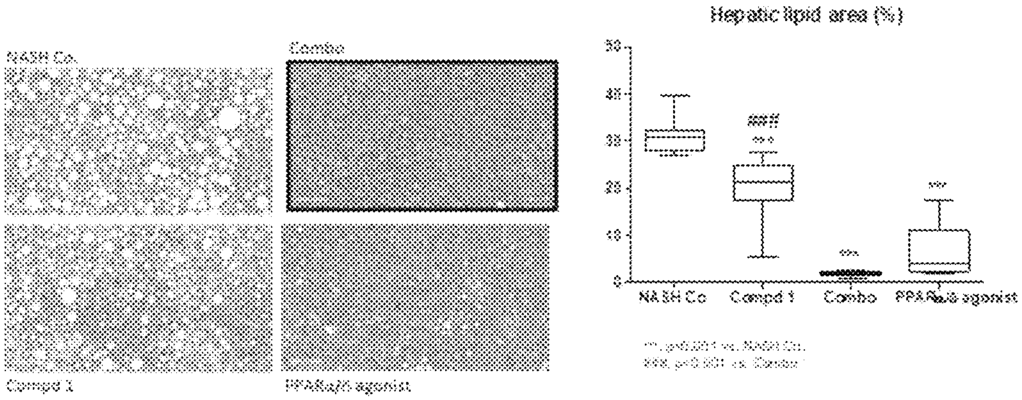
FIG. 5 shows an efficacy of administration in combination with a PPARα/δ agonist by quantifying a relative proportion of lipid droplets in liver tissues after multiple-dose of a drug to mice with induced nonalcoholic steatohepatitis.

For quantitative comparison of fat accumulation in liver tissues, the HE-stained tissues were subjected to an image analysis to calculate a relative proportion of lipid droplets per unit area, thereby evaluating a medicinal efficacy of co-administration. The results thereof are shown in FIGS. 4 and 5.

Figure 6:
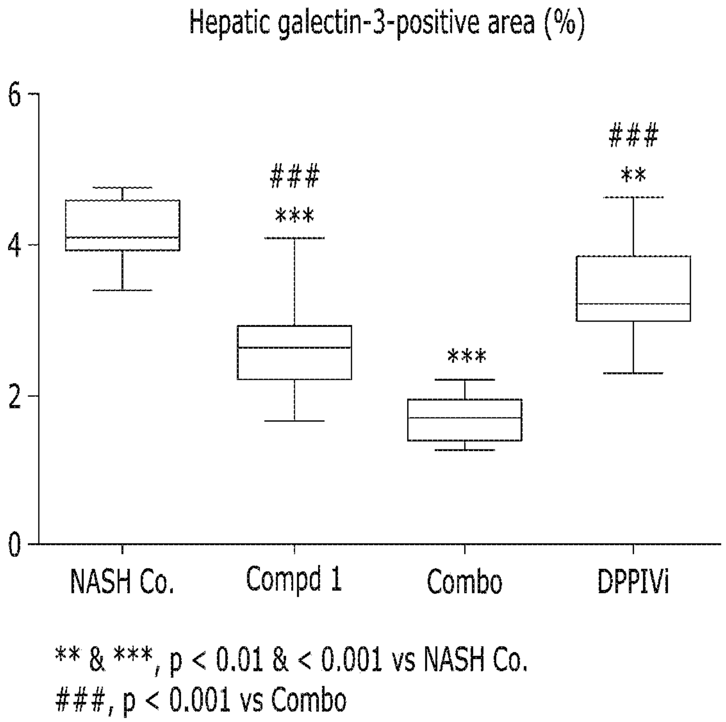
FIG. 6 shows an efficacy of administration in combination with a DPPIV inhibitor on a relative proportion of expression of galectin-3 as an indicator of activated macrophage in liver tissues after multiple-dose administration of a drug to mice with induced nonalcoholic steatohepatitis.
Figure 7:
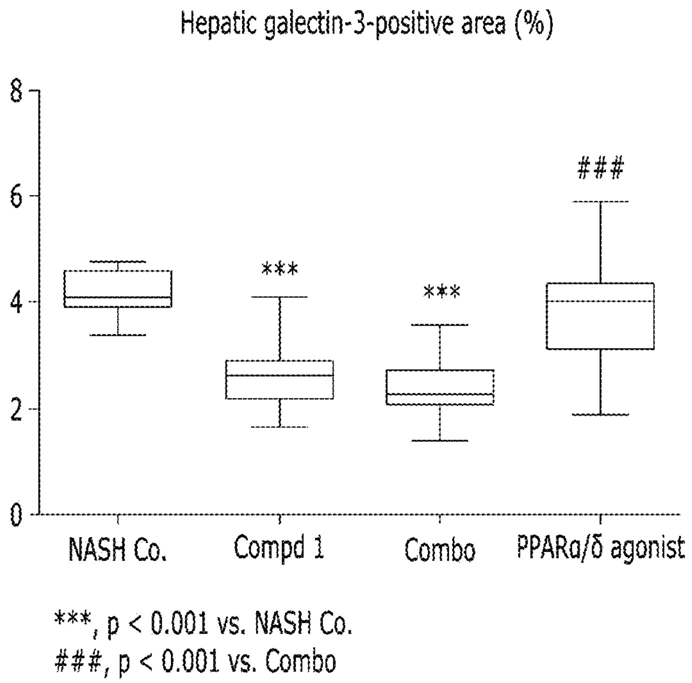
FIG. 7 shows an efficacy of administration in combination with a PPARα/δ agonist on a relative proportion of expression of galectin-3 as an indicator of activated macrophage in liver tissues after multiple-dose administration of a drug to mice with induced nonalcoholic steatohepatitis.

To compare the degree of infiltration of inflammatory cells in liver tissues, an expression level of galectin-3, an indicator of increased expression in activated macrophages, was measured through immunostaining. After that, a ratio of the area stained by the galectin-3 antibody in the unit area was calculated through image analysis so as to evaluate the medicinal efficacy of ameliorating inflammation according to the co-administration. The results thereof are shown in FIGS. 6 and 7.

Figure 8:
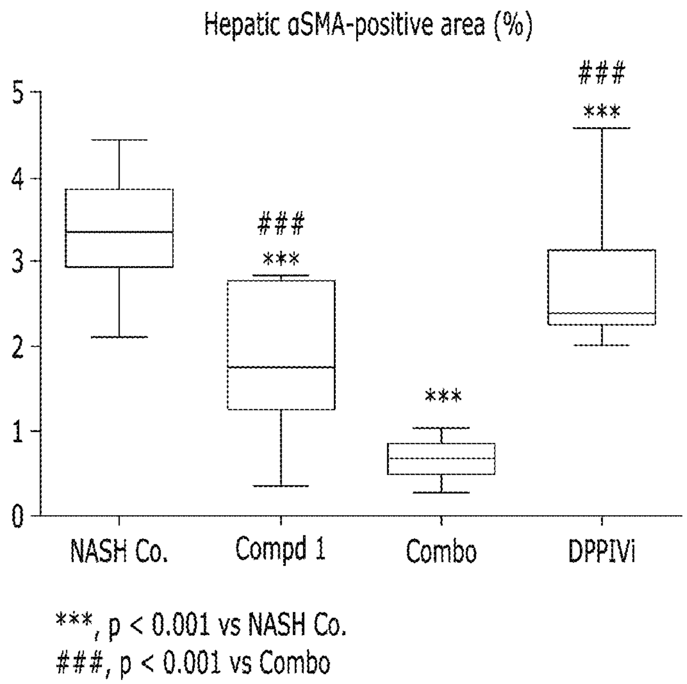
FIG. 8 shows an efficacy of administration in combination with a DPPIV inhibitor on a relative proportion of expression of a smooth muscle actin (αSMA) as an indicator of activated hepatic stellate cells in liver tissues after multiple-dose administration of a drug to mice with induced nonalcoholic steatohepatitis.
Figure 9:
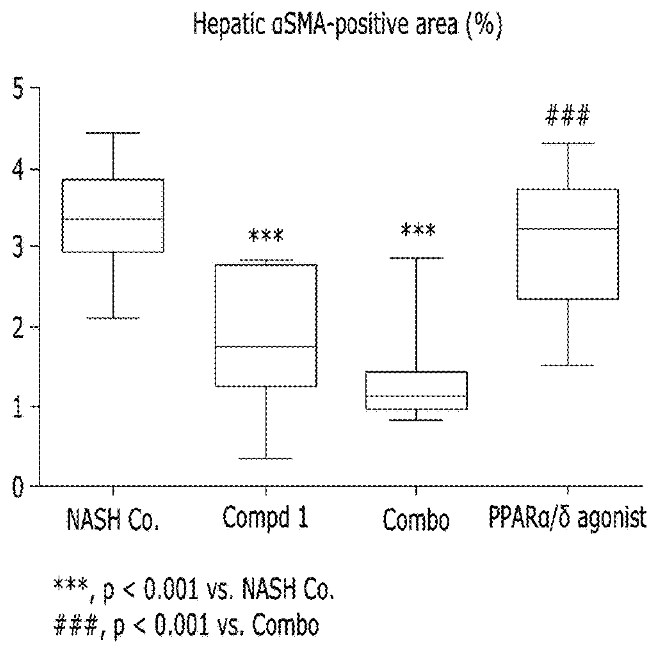
FIG. 9 shows an efficacy of administration in combination with a PPARα/δ agonist on a relative proportion of expression of a smooth muscle actin (αSMA) as an indicator of activated hepatic stellate cells in liver tissues after multiple-dose administration of a drug to mice with induced nonalcoholic steatohepatitis.

To evaluate the effectiveness on fibrosis, an expression of a smooth muscle actin (αSMA) in a liver tissue section was measured through immunostaining so as to compare the ratio of activated stellate cells. After that, a ratio of the area stained by the αSMA antibody in the unit area was calculated through image analysis. The results thereof are shown in FIGS. 8 and 9.

Confirmation of Concentration of Inflammation and Fibrosis-Related Proteins

Figure 10:
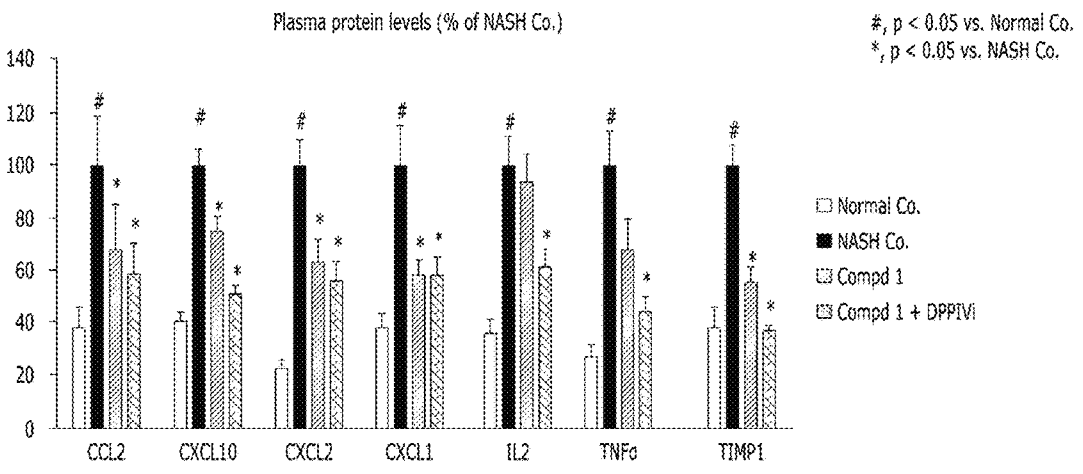
FIG. 10 shows an efficacy of administration in combination with a DPPIV inhibitor on an indicator of inflammation and fibrosis in plasma after multiple-dose administration of a drug to mice with induced nonalcoholic steatohepatitis.

To evaluate an effect on concentration of inflammation (CCL2, CXCl10, CXCl2, IL2 and TNFα) and fibrosis-related protein (TIMP1) in plasma, a concentration of CCL2, CXCl10, CXCl2, IL2, TNFα (MSD, K15255D-1) and TIMP1 (R&D Systems, MTM100) proteins in the plasma obtained from the mouse model was quantified by using a commercially available ELISA kit. The results thereof are shown in FIG. 10.

Measurement of Blood AST and ALT

Figure 11:
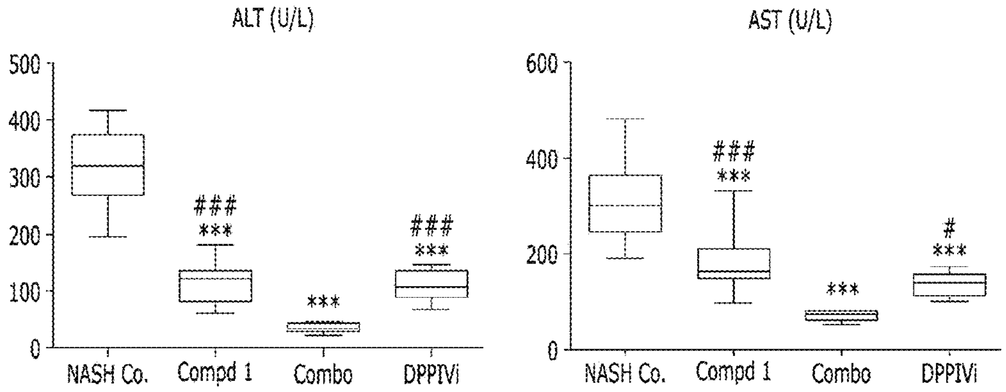
FIG. 11 shows an efficacy of administration in combination with a DPPIV inhibitor on concentration of ALT and AST as an indicator of liver damage in plasma after multiple-dose administration of a drug to mice with induced nonalcoholic steatohepatitis.

The mouse model with induced nonalcoholic steatohepatitis was subjected to autopsy, after which plasma was isolated therefrom, so as to quantify aspartate aminotransferase (AST) and alanine aminotransferase (ALT) by using an automatic blood analyzer (Konelab 20i). The results thereof are shown in FIG. 11.

As confirmed in FIG. 2, the NAS was significantly improved in mice administered with compound 1 alone compared to before treatment, but the effect of administering evogliptin alone, the DPPIV inhibitor, was insignificant. However, when both drugs were administered in combination, the medicinal efficacy of NAS improvement was remarkably increased.

Referring to FIG. 3, when compound 1 or elafibranor (a PPAR agonist), was administered alone, the NAS was significantly improved compared to before treatment, and when both drugs were administered in combination, the medicinal efficacy of NAS improvement was further increased.

Referring to FIG. 4, a size of lipid droplets in liver tissues was decreased in mice administered with compound 1 alone, and thus a relative area of lipid droplets was significantly reduced. When evogliptin, the DPPIV inhibitor, was administered alone, the relative area of lipid droplets showed a tendency of decreasing. Above all, when compound 1 was administered in combination with the DPPIV inhibitor, the relative area of lipid droplets in liver tissues was further reduced, thus confirming an increase in the medicinal efficacy of improving the fatty liver according to the combination of both drugs.

As confirmed in FIG. 5, as a result of quantitatively evaluating a degree of fat deposition in liver tissues, a ratio of fat in liver tissues was significantly reduced by the administration of compound 1 or the PPAR agonist alone. As a result of administering compound 1 in combination with the PPAR agonist, a ratio of lipid droplets area was further reduced, thus showing an improvement of 94% compared to a control group (NASH Co.). This indicates an increase in the medicinal efficacy of improving the fatty liver according to the combination of both drugs.

Referring to FIG. 6, it was shown that an expression of galectin-3, an indicator of activated macrophages in liver tissues, is significantly reduced in mice administered with compound 1 or evogliptin, the DPPIV inhibitor, alone, and when both drugs are used in combination, an effect of decreasing an expression of galectin-3 is further increased. This suggests that when both drugs are administered in combination, an effect of reducing an infiltration of inflammatory cells in liver tissues will be increased.

Referring to FIG. 7, an expression of galectin-3, an indicator of activated macrophages in liver tissues was significantly decreased in mice administered with compound 1 alone. When elafibranor, a PPAR agonist, was administered alone, there was no effect of significantly decreasing an expression of galectin-3, but when both drugs were used in combination, it was confirmed that an effect of reducing an expression of galectin-3 is further increased. This suggests an increase in the effect of reducing an infiltration of inflammatory cells in liver tissues according to the combination of both drugs.

Referring to FIG. 8, an expression of αSMA, which is an indicator of hepatic stellate cell activation inducing fibrosis in liver tissues, was significantly reduced in mice administered with compound 1 or evogliptin, the DPPIV inhibitor, alone. It was suggested that an effect of inhibiting an expression of αSMA is further increased when both drugs are administered in combination. This suggests that an effect of inhibiting fibrosis of liver tissues according to the combination of both drugs is increased.

Referring to FIG. 9, an expression of αSMA, an activation indicator of hepatic stellate cells inducing fibrosis in liver tissues, was significantly reduced in mice administered with compound 1 alone, while there was no effect of significantly reducing an expression of αSMA when elafibranor, the PPAR agonist, was administered alone. However, it was confirmed that an effect of inhibiting an expression of αSMA is further increased when both drugs are administered in combination. This suggests an increase in an effect of inhibiting fibrosis in liver tissues according to the co-administration of both drugs.

FIG. 10 shows that there is an effect on a concentration of blood inflammatory and fibrotic biomarkers when compound 1 is administered alone or in combination with sitagliptin, a DPPIV inhibitor. Plasma concentrations of CCL2, CXCl10 and CXCl2, chemokines that induce an infiltration of inflammatory cells, was increased in NASH mice, and those plasma concentrations thereof were significantly decreased when compound 1 was administered alone. When compound 1 was used in combination with the DPPIV inhibitor, the medicinal efficacy of reducing chemokines was further increased. Inflammatory cytokines, IL2 and TNFα, showed a tendency of decreasing by compound 1 alone, but was significantly decreased when combined with the DPPIV inhibitor. TIMP1, a fibrosis indicator, was also significantly increased in NASH mice, but was significantly decreased by administration of compound 1 alone, and a reduction effect was increased in combination with the DPPIV inhibitor. Accordingly, it is confirmed that an effect of improving plasma inflammatory and fibrotic biomarkers supporting histological changes is increased when compound 1 and the DPPIV inhibitor are used in combination.

FIG. 11 shows an effect of the pharmaceutical composition according to one embodiment on plasma ALT and AST as an indicator of liver damage. When compound 1 or evogliptin, a DPPIV inhibitor, was repeatedly administered alone, plasma concentrations of ALT and AST were significantly reduced. When compound 1 was administered in combination with the DPPIV inhibitor, ALT and AST concentrations were further decreased with a significant difference compared to administration of both drugs alone. This suggests that an effect of preventing damage to hepatocytes caused by nonalcoholic steatohepatitis is increased when compound 1 and the DPPIV inhibitor are administered in combination.

The above results show that administration of the pharmaceutical composition according to one embodiment of the present invention in combination with the GPR119 agonist and an agent for ameliorating metabolic diseases such as the DPPIV inhibitor or the PPAR agonist ameliorates fatty liver and inhibits liver damage, inflammation and fibrosis, thereby providing an effect on nonalcoholic fatty liver disease and exhibiting a more effective therapeutic effect.

<Example 2> Confirmation of Combination Efficacy of GPR119 Ligand and Drugs of Other Mechanisms in Human Macrophages Confirmation of Concentration of Inflammatory Cytokine Proteins Secreted in Medium In order to evaluate in vitro the possibility of increasing an effect of ameliorating inflammation among effects of ameliorating nonalcoholic fatty liver disease according to treatment with the GPR119 ligand in combination with drugs of other mechanisms, inflammatory cytokines in a medium were quantified to confirm an effect of combination of the GPR119 ligand and drugs of other mechanisms on the differentiation of human monocytes.

A human monocyte cell line (THP-1, ATCC® TIB-202™) was treated with 50 ng/ml of phorbol 12-myristate 13-acetate (PMA) for 48 hours and differentiated into macrophages, while being treated with compound 1 in combination with elafibranor as a PPAR agonist, firsocostat as an ACC inhibitor, obeticholic acid as a FXR agonist or cenicriviroc as a CCR2/5 dual antagonist, then replaced with a serum-free medium, and then treated with lipopolysaccharides (LPS; 0.5 ng/ml) for four hours, after which interleukin-1p (IL-1p; R&D Systems, DY201), tumor necrosis factor α (TNFα; R&D Systems, DY210), and C—C motif chemokine ligand 2 (CCL2; R&D Systems, DY279), which are inflammatory cytokines secreted into the medium, were quantified with a commercially available ELISKA kit, so as to evaluate an effect on monocyte differentiation, and the results thereof are shown in FIG. 12.

Figure 12:
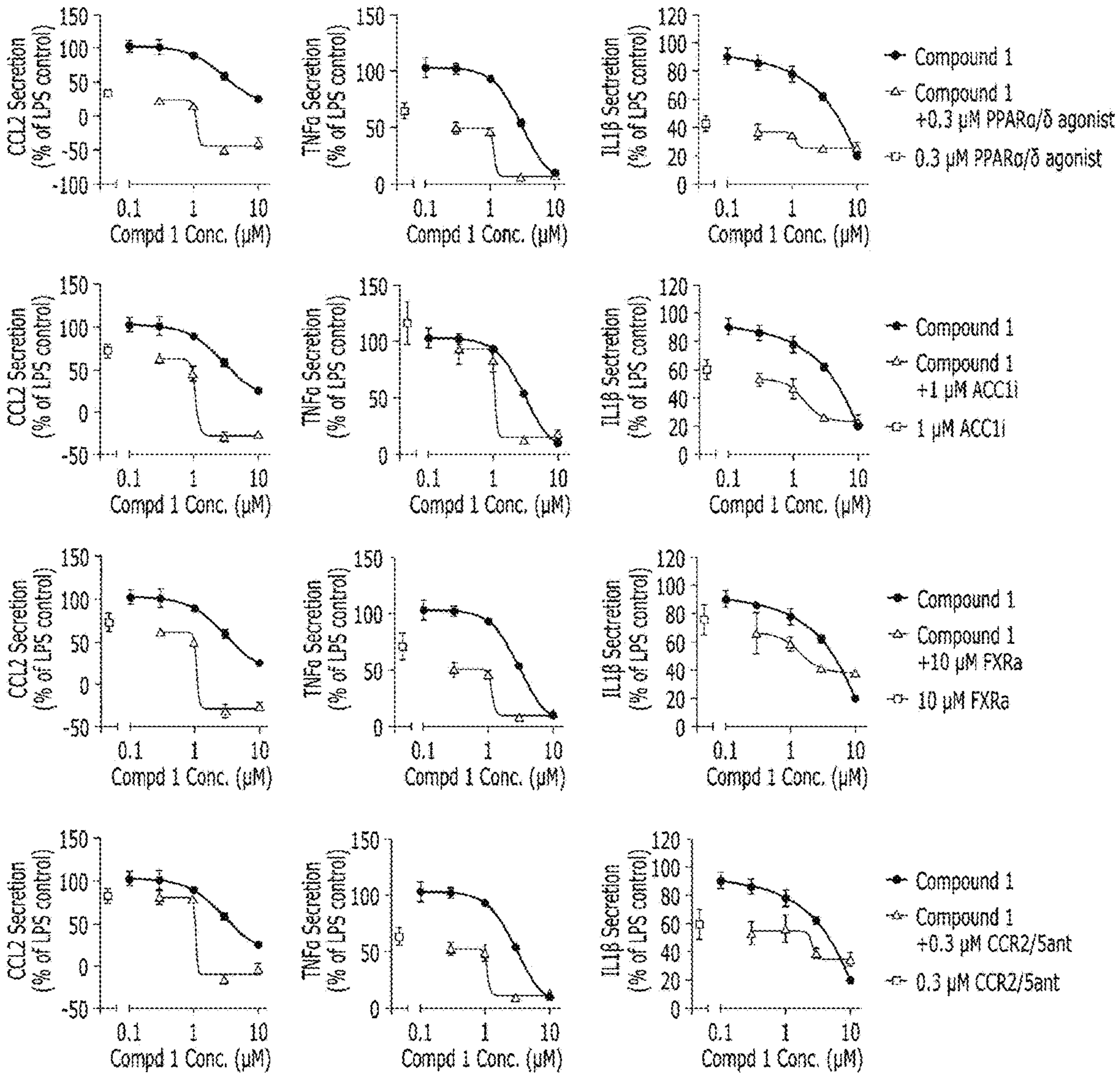
FIG. 12 shows an effect of increasing an inhibitory ability of secretion of CCL2, TNFα and IL1β, which are inflammatory cytokines, by treatment in combination with above compound 1 and a PPARα/δ agonist, an ACC inhibitor, a FXR agonist or a CCR2/5 dual antagonist in a process of differentiating human monocytes into macrophage.

As confirmed in FIG. 12, when treated with compound 1 of the present invention during the process of differentiation of monocytes into macrophages, it was confirmed that IL-1β, TNFα and CCL2 secretion according to macrophage activation was decreased in a concentration-dependent manner. When treated with the PPAR agonist, the ACC inhibitor, the FXR agonist or the CCR2/5 dual antagonist in combination, an inhibitory ability of compound 1 on inflammatory cytokine secretion was increased.

The above results indicate that compound 1 of the present invention inhibits differentiation of immune cells and suppresses secretion of inflammatory cytokines caused by innate immunity, thereby inhibiting the progression of nonalcoholic fatty liver disease, and thus this action may be increased when treated in combination with the PPAR agonist, the ACC inhibitor, the FXR agonist or the CCR2/5 dual antagonist.

<Example 3> Confirmation of Combination Efficacy of GPR119 Ligand and Drugs of Other Mechanisms in Human Hepatic Stellate Cells Confirmation of Expression Level of Fibrotic Protein Expressed in Cells In order to evaluate in vitro the possibility of increasing an effect of inhibiting fibrosis among effects of ameliorating nonalcoholic fatty liver disease according to co-treatment of the GPR119 ligand and drugs of other mechanisms, a concentration of fibrotic proteins expressed in primary human hepatic stellate cells was quantified.

Figure 13:
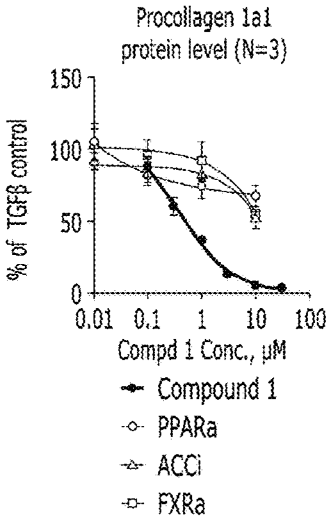
FIG. 13 shows an effect of increasing an ability to decrease an expression of fibrotic proteins by treatment in combination with above compound 1 and a PPARα/δ agonist, an ACC inhibitor or a FXR agonist in a process of activating primary human hepatic stellate cells with TGFβ.

Primary human hepatic stellate cells (ScienCell, #5300) were stabilized for 24 hours, then cultured in a serum-free medium for 24 hours, and then treated with compound 1 in combination with elafibranor as a PPAR agonist, firsocostat as an ACC inhibitor, or obeticholic acid as a FXR agonist together with 5 ng/ml of recombinant tumor growth factor β1 (TGFβ1), after which the resulting cells were harvested in 18 hours later and an amount of pro-collagen 1a1 in total cell proteins was quantified with a commercialized ELISKA Kit (R&D Systems, DY6220), while an amount of total cell proteins was quantified and corrected by a BCA method, and the results of calculating a concentration response curve of each drug and a concentration ($IC_{30}$) showing 30% inhibitory activity are shown in FIG. 13.

As can be confirmed from FIG. 13, when compound 1 was treated alone, a protein expression of pro-collagen 1a1 induced by TGFβ 1 was inhibited in a concentration-dependent manner, and a 30% inhibitory concentration was calculated to be 0.55 μM. The PPAR agonist, the ACC inhibitor or the FXR agonist showed a relatively low response. The 0.3 μM of above compound 1 was treated along with the PPAR agonist, the ACC inhibitor or the FXR agonist at a concentration expected to induce 30% inhibition upon co-treatment, so as to calculate a concentration at which an expression of procollagen 1a1 is inhibited 30%, and calculate a fraction of concentration at which both drugs exhibit 30% inhibitory activity when co-treated compared to when treated with each drug alone, so that a sum thereof is expressed as a combination index (CI) (Chou T C & Talalay P., Adv Enzyme Regul, 1984:22:27-55). When compound 1 was treated in combination with the PPAR agonist or the ACC inhibitor, the CI was calculated to be 0.7 and 0.6, which was smaller than 1, thus confirming a synergistic effect. And the CI was calculated to be 1 when treated in combination with the FXR agonist, thus confirming an additive effect.

The above results indicate that compound 1 of the present invention inhibits activation of hepatic stellate cells to suppress expression of collagen, which is a fibrosis protein, thereby inhibiting the progression of nonalcoholic fatty liver disease, and thus this action may be increased when treated in combination with the PPAR agonist, the ACC inhibitor or the FXR agonist.

The invention claimed is:

1. A method for preventing or treating nonalcoholic fatty liver disease, the method comprising:

administering a therapeutically effective amount of a pharmaceutical composition including, a compound represented by chemical Formula 1, a pharmaceutically acceptable salt thereof, an optical isomer thereof, a hydrate thereof, a solvate thereof, or mixtures thereof; and at least one selected from a PPAR agonist, a DPPIV inhibitor, an ACC inhibitor, a FXR agonist and a CCR2/5 dual antagonist as an active ingredient to a subject in need of treatment,

[Formula 1]

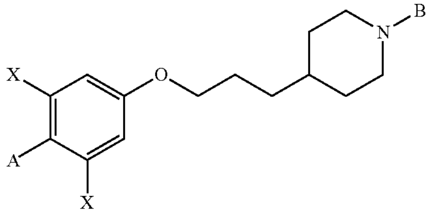

wherein in above Formula 1,

A is an oxadiazole group, a dihydrooxazole group, a thiazole group or a thiadiazole group, in which above A is unsubstituted or substituted with at least one substituent selected from the group consisting of a halogen atom, a C1-C6 straight or branched chain alkyl group, and a C1-C6 straight or branched chain hydroxyalkyl group, in which the alkyl group or the hydroxyalkyl group is each independently unsubstituted or substituted with a halogen atom or a C1-C6 alkoxy group;

B is a pyridine group, a pyrimidine group, a pyrazine group or an oxadiazole group, in which above B is unsubstituted or substituted with at least one substituent selected from the group consisting of a halogen atom, a C1-C6 straight or branched chain alkyl group, a C1-C6 straight or branched chain hydroxyalkyl group, a C1-C6 alkoxy group and an oxadiazole group, in which the C1-C6 straight or branched chain alkyl group, the C1-C6 straight or branched chain hydroxyalkyl group, the C1-C6 alkoxy group or the oxadiazole group is each independently unsubstituted or substituted with halogen, a C1-C6 alkyl group or a C1-C6 alkoxy group; and X is F, Cl, Br or I.

2. The method according to claim 1, wherein above A is

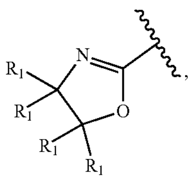,
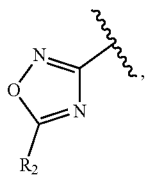,
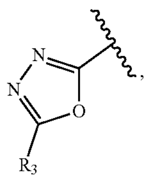,
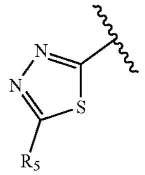
or
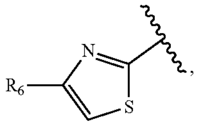, and $R_1$ to $R_3$, $R_5$ and $R_6$ are each independently at least one substituent selected from the group consisting of a hydrogen atom, a halogen atom, a C1-C6 straight or branched chain alkyl group and a C1-C6 straight or branched chain hydroxyalkyl group, in which the alkyl group or the hydroxyalkyl group is each independently unsubstituted or substituted with a halogen atom or a C1-C6 alkoxy group.

3. The method according to claim 1, wherein above B is

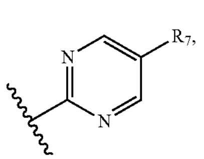
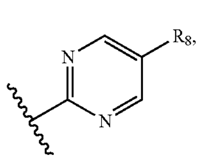
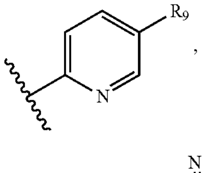
,
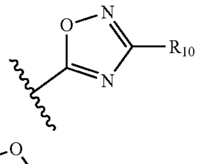
or
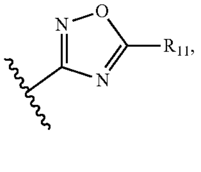

and $R_7$ to $R_{11}$ are each independently substituted with at least one substituent selected from the group consisting of a hydrogen atom, a halogen atom, a C1-C6 straight or branched chain alkyl group, a C1-C6 straight or branched chain hydroxyalkyl group, a C1-C6 alkoxy group and an oxadiazole group, in which the alkyl group, the hydroxyalkyl group, the alkoxy group or the oxadiazole group is each independently unsubstituted or substituted with a halogen atom, a C1-C6 alkyl group or a C1-C6 alkoxy group.

4. The method according to claim 1, wherein X is F.

5. The method according to claim 1, wherein above A is an oxadiazole group substituted with a C1-C6 straight or branched chain alkyl group, above B is a pyrimidine group substituted with a C1-C6 straight or branched chain alkyl group, and X is F.

6. The method according to claim 1, wherein the compound represented by above formula 1 is 3-(4-(3-(1-(5-ethylpyrimidin-2-yl) piperidin-4-yl) propoxy)-2,6-difluorophenyl)-5-isopropyl-1,2,4-oxadiazole.

7. The method according to claim 6, wherein the pharmaceutical composition comprises the PPAR agonist, the DPPIV inhibitor, the ACC inhibitor, the FXR agonist and the CCR2/5 dual antagonist.

8. The method according to claim 6, wherein the pharmaceutical composition comprises at least one of elafibranor, evogliptin, sitagliptin, firsocostat, obeticholic acid and cenicriviroc.

9. The method according to claim 8, wherein the PPAR agonist is elafibranor.

10. The method according to claim 8, wherein the DPPIV inhibitor is at least one of evogliptin and sitagliptin.

11. The method according to claim 8, wherein the ACC inhibitor is firsocostat.

12. The method according to claim 8, wherein the FXR agonist is obeticholic acid.

13. The method according to claim 8, wherein the CCR2/5 dual antagonist is cenicriviroc.

14. The method according to claim 1, wherein the non-alcoholic fatty liver disease is selected from the group consisting of simple fatty liver, nonalcoholic steatohepatitis, liver fibrosis and cirrhosis.

15. The method according to claim 1, wherein the pharmaceutical composition inhibits deposition of triglycerides in liver tissues.

16. The method according to claim 1, wherein the pharmaceutical composition inhibits occurrence of inflammation in liver tissues.

17. The method according to claim 1, wherein the pharmaceutical composition inhibits fibrosis of liver tissues.

18. A pharmaceutical composition for preventing or treating nonalcoholic fatty liver disease comprising:

a compound represented by chemical Formula 1, a pharmaceutically acceptable salt thereof, an optical isomer thereof, a hydrate thereof, a solvate thereof or mixtures thereof; and at least one selected from a PPAR agonist, a DPPIV inhibitor, an ACC inhibitor, a FXR agonist and a CCR2/5 dual antagonist:

[Formula 1]

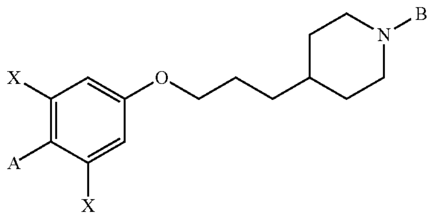

wherein in above Formula 1,

A is an oxadiazole group, a dihydrooxazole group, a thiazole group or a thiadiazole group, in which above A is unsubstituted or substituted with at least one substituent selected from the group consisting of a halogen atom, a C1-C6 straight or branched chain alkyl group, and a C1-C6 straight or branched chain hydroxyalkyl group, in which the alkyl group or the hydroxyalkyl group is each independently unsubstituted or substituted with a halogen atom or a C1-C6 alkoxy group;

B is a pyridine group, a pyrimidine group, a pyrazine group or an oxadiazole group, in which above B is unsubstituted or substituted with at least one substituent selected from the group consisting of a halogen atom, a C1-C6 straight or branched chain alkyl group, a C1-C6 straight or branched chain hydroxyalkyl group, a C1-C6 alkoxy group and an oxadiazole group, in which the C1-C6 straight or branched chain alkyl group, the C1-C6 straight or branched chain hydroxyalkyl group, the C1-C6 alkoxy group or the oxadiazole group is each independently unsubstituted or substituted with halogen, a C1-C6 alkyl group or a C1-C6 alkoxy group; and X is F, Cl, Br or I.

* * * * *